United States Patent [19]
Tamura et al.

[11] Patent Number: 5,617,856
[45] Date of Patent: Apr. 8, 1997

[54] BIOLOGICAL INFORMATION-MEASURING APPARATUS

[75] Inventors: Itsuro Tamura, Kawachinagano; Atsushi Iida, Osaka; Tsutomu Takae, Osaka; Masao Wada, Osaka, all of Japan

[73] Assignee: Osaka Gas Company Limited, Japan

[21] Appl. No.: 308,731

[22] Filed: Sep. 19, 1994

[30]  Foreign Application Priority Data

Sep. 24, 1993  [JP]  Japan .................................. 5-238385
Sep. 24, 1993  [JP]  Japan .................................. 5-238389

[51] Int. Cl.⁶ ................................................. A61B 5/05
[52] U.S. Cl. ....................... 128/653.1; 324/248; 324/261
[58] Field of Search ........................... 128/653.1, 653.2, 128/653.5; 324/248, 226, 260, 261, 262

[56]  References Cited

U.S. PATENT DOCUMENTS

| 3,557,777 | 1/1971 | Cohen ................................... 128/653.1 |
| 4,816,760 | 3/1989 | Svegander et al. ...................... 324/226 |
| 5,018,724 | 5/1991 | Naser et al. .......................... 128/653.1 |
| 5,152,288 | 10/1992 | Hoenig et al. . |
| 5,265,611 | 11/1993 | Hoenig et al. ......................... 128/653.1 |

FOREIGN PATENT DOCUMENTS

| 0277283 | 8/1988 | European Pat. Off. ............ 128/653.1 |
| 4300564 | 8/1993 | Germany . |
| 2-116767 | 5/1990 | Japan . |
| 4061819 | 7/1994 | Japan ................................... 128/653.1 |

*Primary Examiner*—Marvin M. Lateef
*Assistant Examiner*—Brian L. Casler
*Attorney, Agent, or Firm*—Dilworth & Barrese

[57]  ABSTRACT

A biological information-measuring apparatus which is situated in a shielded room and includes measuring means for measuring biological information of a subject arranged and supported between a pair of supporting pillars of a double housing type support, wherein H-cross section members are combined to form a lattice-like supporting frame, and the bottoms of the supporting pillars are anchored to the members forming the supporting frame.

10 Claims, 23 Drawing Sheets

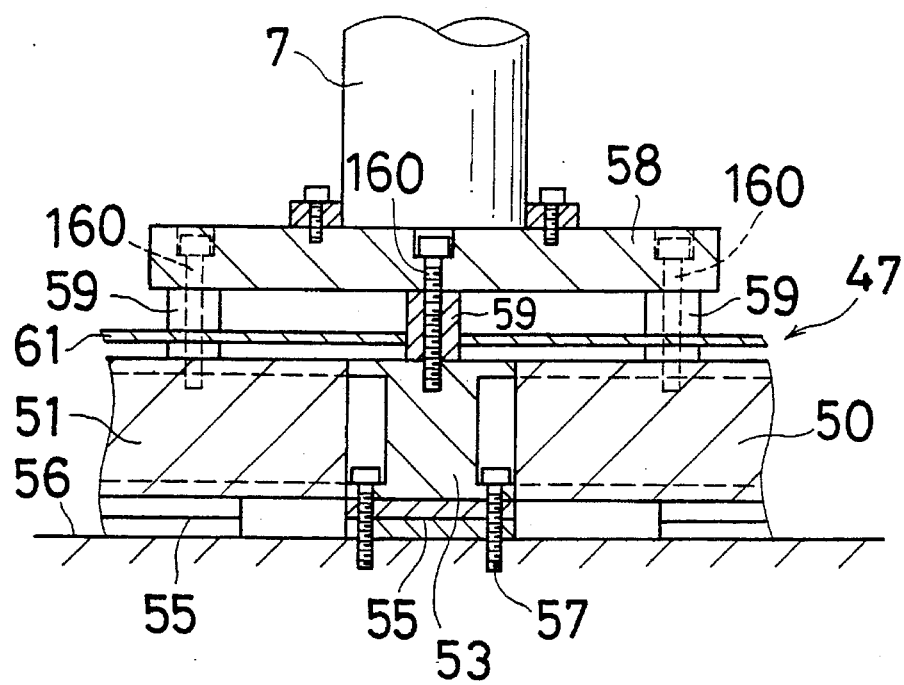
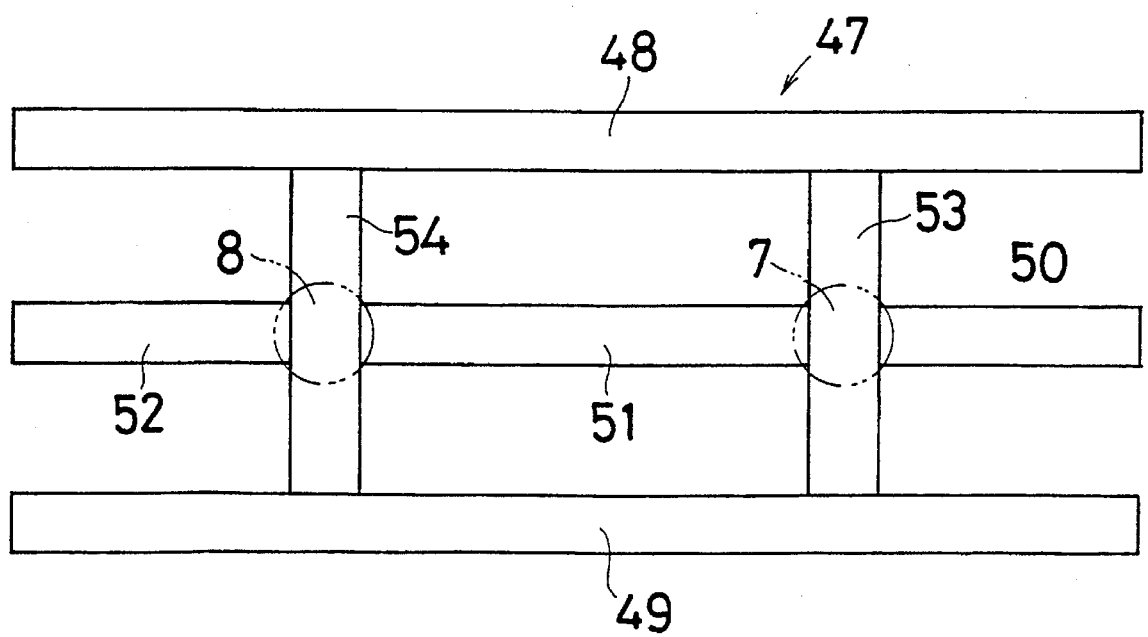
FIG. 3

X: 27.75Hz
Y: 29.57dBEU/EU

BIOLOGICAL INFORMATION-MEASURING APPARATUS

BACKGROUND OF THE INVENTION

1. Field of the Invention

The present invention relates to an apparatus for detecting and measuring various biological information generated by the body of a subject, and particularly it relates to a biomagnetic field-measuring apparatus for measuring at a high precision the strength of weak magnetic fields generated by organs such as the brain, arms, eyeballs and heart.

2. Description of the Related Art

The human body generates a variety of biological information in response to changes in the external environment, and as used herein, the term "biological information" refers not only to physiological quantities generated by the body, but also includes the absorption of X-rays and magnetism.

An X-ray tomographic apparatus, known as an X-ray CT scanner, provides two-dimensional cross-sectional images from the X-ray absorption-.of sections of the body, and the images enable the diagnosis of diseases of the head and abdomen.

A magnetic resonance computed tomography apparatus, known as an MRI apparatus, provides information on the resonance absorption of hydrogen or carbon atoms, which reflects their electronic state, particularly enabling the diagnosis of oncocytes.

Biomagnetic field-measuring apparatuses, also known as MEG apparatuses, detect extremely weak biomagnetism of $10^{-12}$ T or less from human organs, and they are useful for preparing magnetoencephalograms and magnetoencephalograms and may thus be used for the diagnosis of epilepsy, encephalopathy, etc. These measuring apparatuses are all weighty, especially biomagnetic field-measuring apparatuses which have a total of weight of about 200 kgf.

In general, supporting means suspends biomagnetic field-measuring means from the ceiling, which is more subject vibration than the floor, and whose vibration is difficult to prevent.

Another typical prior technique employs a construction in which magnetic field-measuring means is mounted on an rocking arm anchored to the wall, etc. of a magnetically shielded room. With this technique, it is difficult to support the magnetic field-measuring means so that it does not vibrate.

Also, in an embodiment disclosed in Japanese Unexamined Patent Publication (KOKAI) JP-A 2-116767 (1990), the foundation of the magnetically shielded room is enlarged, and a supporting pillar is provided to directly connect the foundation of the magnetically shielded room with the supporting means. This construction is a very effective means of preventing vibration, but there is no mechanical connection between the magnetically shielded room and the supporting means, and thus the rigidity and mass of the magnetically shielded room are not efficiently utilized. Furthermore, a large hole must be made in the magnetically shielded room, and this result in lower shielding performance.

Since only a portion of the magnetic fields has conventionally been sampled when measuring biomagnetic fields, a requisite has been an increase in the degree of freedom of the supporting means which supports the biomagnetic field-measuring means which detects the magnetic field, and consequently it has been difficult to increase the frequency of vibration of the normal mode of the supporting means.

With this type of biomagnetic field-measuring apparatus, when detecting the strength of magnetic fields generated from the body using a fluxmeter which employs a superconducting quantum interference device (SQUID), when the fluxmeter vibrates undesirably it moves across the surrounding magnetic field, thus generating noise. Therefore, controlling the amplitude of the fluxmeter so that it does not vibrate results in controlling the noise. The vibration energy is proportional to the square of the amplitude and the square of the frequency. By raising the frequency (natural) to greatly reduce the amplitude, it is possible to lower the level of noise.

SUMMARY OF THE INVENTION

It is an object of the invention to provide a biological information-measuring apparatus capable of preventing the vibration of the biological information-measuring means and thus reducing the level of noise.

The invention provides a biological information-measuring apparatus which is situated in a shielded room, and comprises measuring means for measuring biological information of a subject situated and supported between a pair of supporting pillars of a double housing type support, characterized in that H-cross section members are combined to form a lattice-like supporting frame, and the bottoms of the supporting pillars are anchored to the members forming the support frame.

The invention further provides a biological information-measuring apparatus which is situated in a shielded room,
 characterized in that the proximal ends of a pair of parallelly spaced arms disposed between the pair of supporting pillars of the double housing type support are anchored to the wall of the shielded room at an anchoring position, so as to be able to pivot around the horizontal axis;
 measuring means for measuring biological information of a subject is provided at the free distal ends of the arms, so as to allow angular displacement around an axis parallel to the horizontal axis; and
 the pair of arms are connected by a connecting member.

The invention is also characterized in that means are provided for anchoring the arms and the magnetic measuring means in a detachable manner.

The invention is further characterized in that the mounting piece at the top of the free distal end of each arm is anchored to the arm body in a detachable manner, and the supporting shaft for the measuring means is held for support in a support hole sandwiched vertically between the mounting piece and the arm body.

The invention is yet further characterized in that the top sections of screws inserted and threadedly engaged with the supporting pillars in a direction perpendicular to its axis are tapered, and the top sections thereof match depressions whose inner diameters become smaller as they approach the bases formed on the sides of the arms, to anchor the arms to the supporting pillars.

The invention is still further characterized in that the proximal ends of the arms can be anchored to brackets anchored to anchoring positions, using bolts.

The invention provides a biological information-measuring apparatus which is situated in a shielded room,
 characterized by comprising a double housing type support with a pair of supporting pillars;

measuring means situated between the supporting pillars, for measuring biological information of a subject;

means for adjusting the measuring means by angular displacement at a measuring position around a horizontal axis; and a bed which supports and changes the vertical position of the subject.

According to the invention, the measuring means is characterized by being supported by the supporting pillars at a maintenance position lower than the measuring position.

The supporting means of the invention is characterized by being supported at any three sides of the shielded room, the ceiling, floor or wall, to allow utilization of the rigidity of the shielded room to increase the frequency of vibration of the normal mode of the supporting means, and preferably the supporting means is supported at the ceiling and floor of the shielded room, and the arms are supported at the wall of the shielded room.

The measuring means of the invention is preferably selected from the group consisting of biomagnetic field-measuring means, MRI apparatuses and X-ray CT scanners.

The biological information available for use according to the invention is most preferably a biomagnetic field, and the measuring means biomagnetic field-measuring means. The biomagnetic field is particularly preferred to be a brain magnetic field.

According to the invention, the frequency of vibration of the normal mode of the supporting, means which supports the biological information-measuring means is characterized by being about 10 Hz or greater, preferably about 25 Hz or greater, and more preferably about 30 Hz or greater.

These and other objects will become more apparent from the following description and drawings.

BRIEF DESCRIPTION OF THE DRAWINGS

Other and further objects, features, and advantages of the invention will be more explicit from the following detailed description taken with reference to the drawings wherein:

FIG. 2 is a sectional view of a part of a supporting frame according to the invention;

FIG. 3 is a plane view of the supporting frame shown in FIG. 2;

DETAILED DESCRIPTION OF THE PREFERRED EMBODIMENTS

Figure 1:
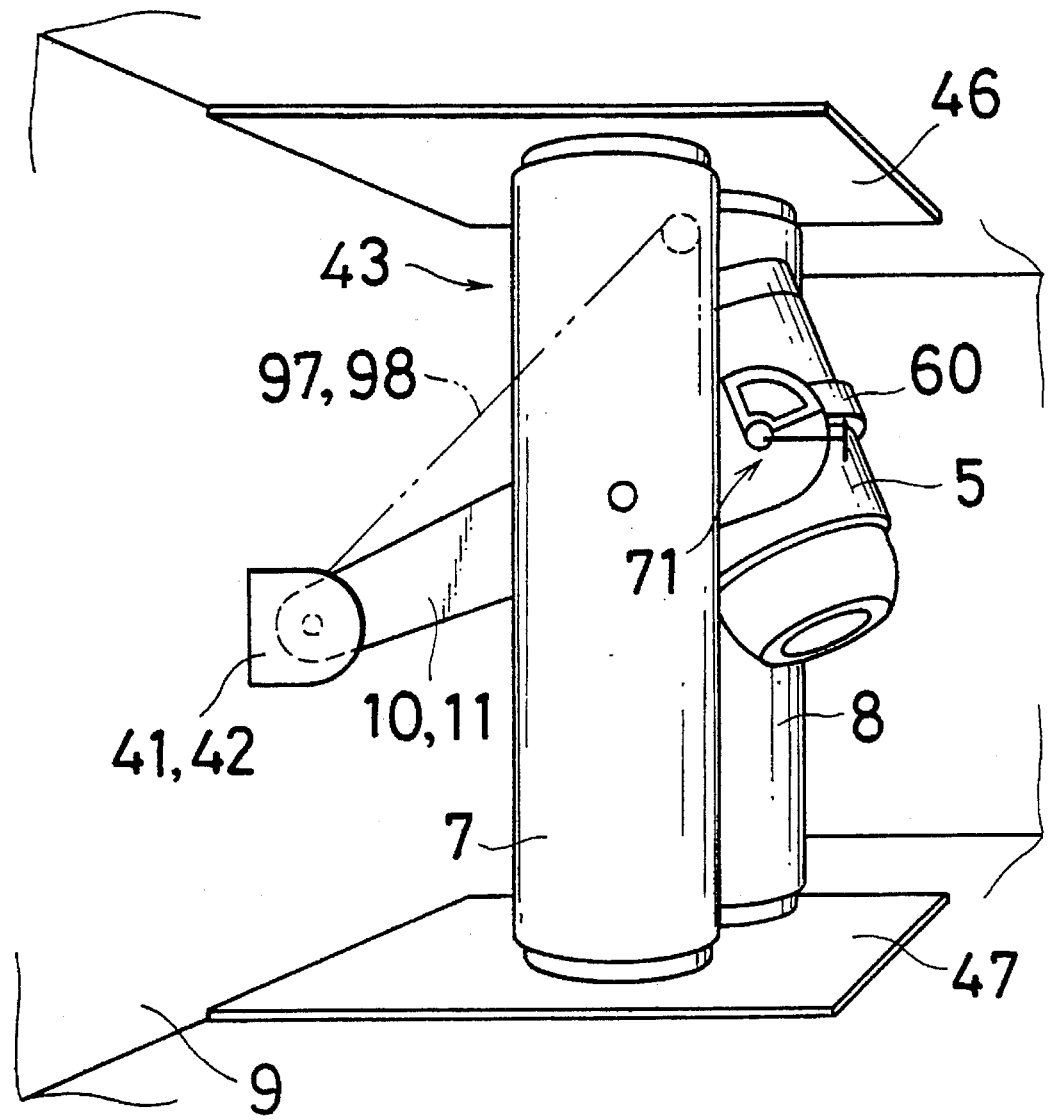
FIG. 1 is a perspective view of a biomagnetic field-measuring apparatus according to an embodiment of the invention.

Now referring to the drawings, preferred embodiments of the invention are described below.

For explanation of a preferred embodiment of the invention, the following description is made only with reference to a biomagnetic field-measuring apparatus as an example of a biological information-measuring apparatus, but this is merely an example for exemplification and easier understanding of the invention. It will be readily apparent to those skilled in the art that application of the biological information-measuring apparatus according to the invention is not, however, limited to biomagnetic field-measuring apparatuses, and the invention may be carried out with other measuring apparatuses, such as those relying on MRI, X-ray CT, and the like.

In FIG. 1, magnetic field-measuring means 5 for detecting a weak magnetic field generated from the body, for example the brain, of a subject, is provided at the free distal ends of a pair of arms 10, 11 so as to be pivotable by angular displacement around the horizontal axis, and the proximal ends of the arms 10, 11 are mounted on the wall 9 of a magnetically shielded room of a building via brackets 41, 42, so as to be pivotable around the horizontal axis. A pair of supporting pillars 7, 8 are provided to maintain the pivoting angle of the arms 10, 11 after it is set. The top ends of the supporting pillars 7, 8 are anchored to a ceiling board 46, and the pair of supporting pillars 7, 8 and the ceiling board 46 connecting their top ends form a double housing type support 43. The bottom ends of these supporting pillars 7, 8 are anchored to a supporting frame 47. The magnetic measuring means 5 comprises a superconducting quantum interference device (SQUID) type fluxmeter 4 immersed in liquid helium stored in a cryogenic vessel (Dewar flask), and this magnetic measuring means 5 has a heavy weight of, for example, 200 kgf.

A SQUID has a construction wherein one or two Josephson junctions are combined with a superconducting ring, to allow high precision measurement of the strength of a weak magnetic field emanating from the body, for example a human brain, arm, eyeball or heart. Brain magnetism is on the order of about 1/100 of the magnetic field of the heart or eyeball, and thus its measurement requires a particularly high-precision apparatus. When the brain receives any stimulus or initiates even a slight thought, the neurons are activated and a current flows. This brain-activated current induces a magnetic field. Consequently, when the brain magnetic field is measured, it is possible to identify at what section of the brain the current has flowed.

FIG. 2 is a sectional view which shows a construction wherein the supporting pillar 7 is anchored to the supporting frame 47, and FIG. 3 is a plane view of the supporting frame 47. The supporting frame 47 is constructed as a lattice by assembling a pair of parallel longitudinal members 48, 49, parallel intermediate members 50, 51, 52 between them, and lateral members 53, 54 which cross perpendicular to the members 48 to 52. The cross section of each of the members 48 to 54 is H-shaped, and they are made of, for example, aluminum. "H-shaped" should be interpreted to include "I-shaped" and similar shapes as well. The supporting frame 47 is situated on the floor 56 of the magnetically shielded room via a liner or spacer 55 made of a non-magnetic material such as aluminum, and it is anchored to the floor 56 with an anchor bolt 57. The anchor bolt 57 is also made of a non-magnetic material such as aluminum or a synthetic resin.

A base plate 58 to which the bottom of the supporting pillar 7 is anchored, is in turn anchored to the supporting frame 47 by a bolt 160 via the spacer 59.

Figure 4:
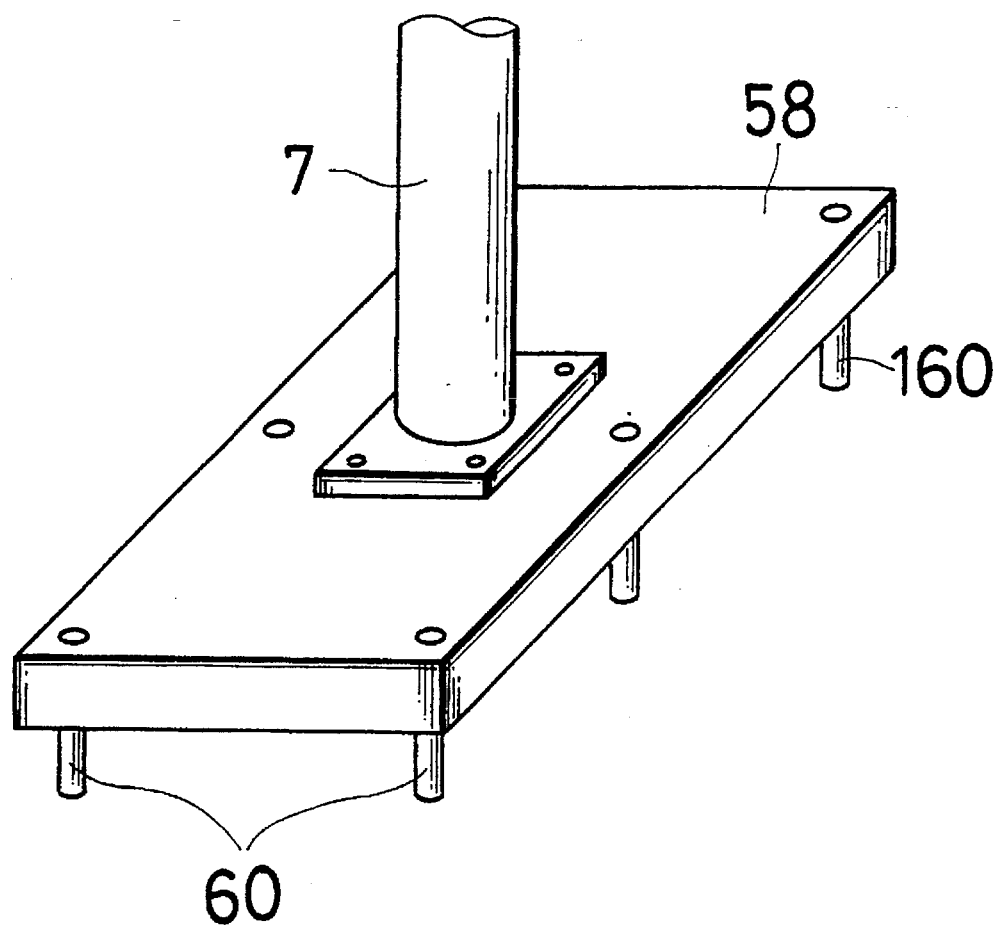
FIG. 4 is a perspective view showing the state of a supporting pillar whose bottom is anchored to a base plate.

FIG. 4 is a perspective view of the base plate 58. As mentioned above, the bolt 60 is inserted into the flat base plate 58. The base plate 58 may be made of fiber-reinforced plastic, aluminum or the like, and the spacer 59 may be made of a material such as fiber-reinforced plastic (abbrev: FRP). A magnetic shielding plate 61 is situated on the supporting frame 47 below the base plate 58. The magnetic shielding plate 61 is made of, for example, permalloy or the like, and has a thickness of 1 to 2 mm.

By using this type of supporting frame 47, even when a large weight is pressing on the supporting frame 7, the supporting frame 47 bends (the degree of bending δ of the section is less than 0.2 mm, e.g. a few dozen μm), the supporting pillar 7 is prevented from deforming downward, thus allowing a "footing" to be secured, and consequently allowing the frequency of vibration of the normal mode of the supporting frame and double housing type supporter to be about 25 Hz or greater, which sufficiently lowers the amplitude of the supporting pillar 7 to reduce the level of noise included in the detection signal of the biomagnetic field. The construction is the same for the other supporting frame 8.

Using the construction of the supporting pillar 7 and supporting frame 47 shown in FIG. 2, when a brain magnetic field-measuring apparatus according to the invention which has a total weight of about 628 kg is supported, the degree of bending (sinking) of the section is calculated to be about 3.4μ.

For example, the supporting frame is anchored to the ceiling and floor of a shielded room or other type of room, and arms are anchored to the wall. This 3-way anchoring system easily allows a frequency of vibration of the normal mode of 10 Hz in other directions as well.

Because the arms are anchored to the wall, the bending in the direction parallel to the arms may be sufficiently reduced, and the frequency of vibration of the normal mode may easily be as much as about 10 Hz or higher, or about 25 Hz or higher.

Furthermore, by increasing the section modulus of the supporting pillar, and anchoring the supporting pillar onto the ceiling and floor of the shielded room or other room, it is easily possible to increase the frequency of vibration of the normal mode in the direction perpendicular to the arms to about 10 Hz or greater even with heavy magnetic field-measuring apparatuses. For example, when the frequency of vibration of the normal mode is calculated fox a case where the outer diameter of the supporting pillar is 250 mm, the inner diameter is 210 mm, GFRP (Young's modulus: 1500 kg/mm$^2$) is used as the material and the length of the supporting pillar is 2400 mm, the frequency of vibration of the normal mode is as high as about 25 Hz even when supporting a 200 kg magnetic field-measuring means and a 250 kg load of the arms.

The supporting means used is mainly made of a non-metallic, non-magnetic material such as fiber-reinforced plastic (FRP). This further reduces the generation of noise due to an eddy current, to avoid the generation of noise.

According to the invention, the frequency of vibration of the normal mode of the supporting means of the biomagnetic field-measuring apparatus is set to about 10 Hz or greater, preferably about 25 Hz or greater, and more preferably about 30 Hz or greater, for the following reasons.

As mentioned above, by setting a high frequency of vibration of the normal mode of the supporting means, it is possible to greatly lower the amplitude, and thus reduce the level of noise. The peak vibration is lowered in inverse proportion to the square of the frequency of vibration of the normal mode. Consequently, when the amplitude is lowered, the noise generated by the vibration is likewise reduced.

Figure 26:
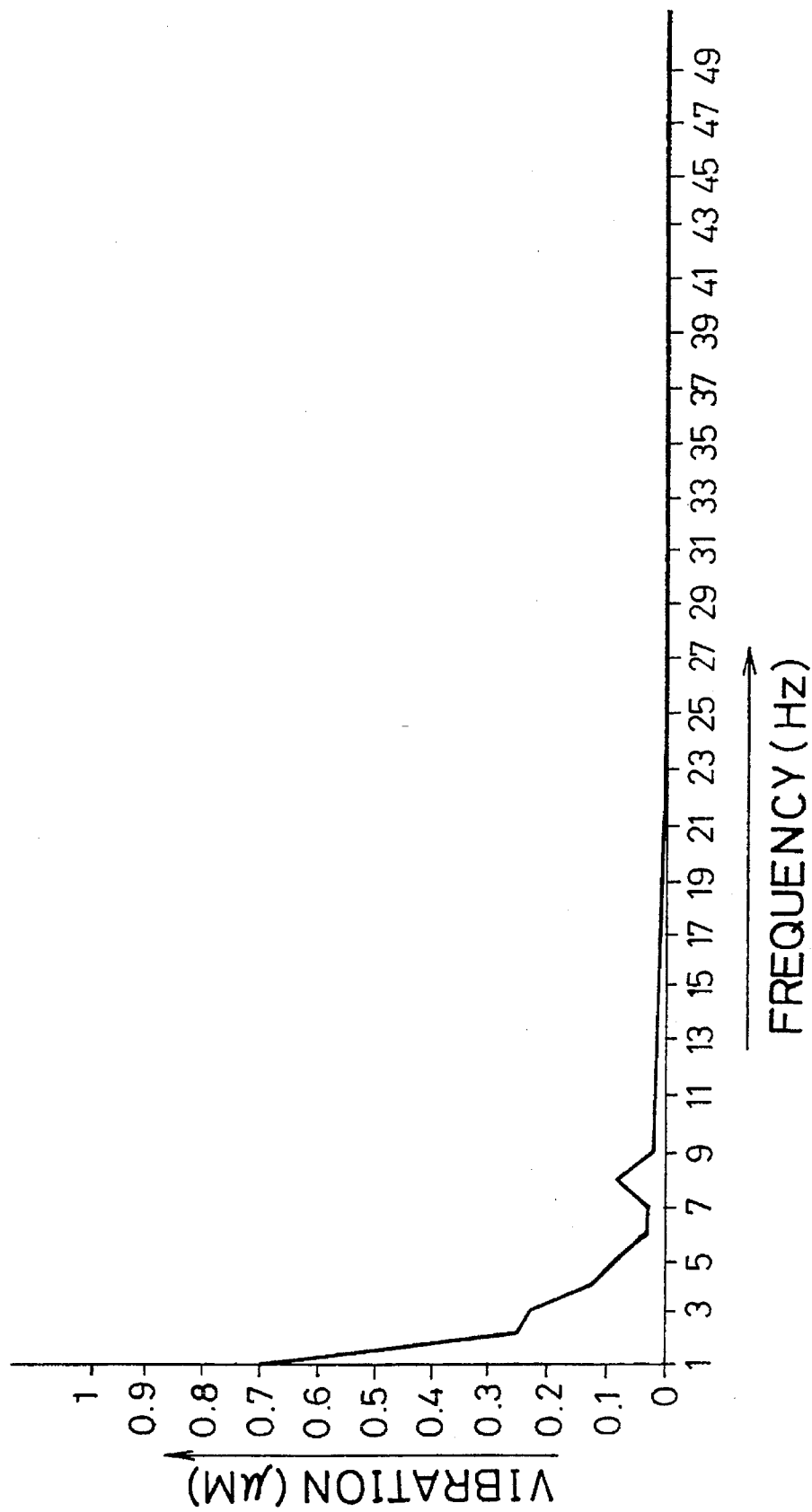
FIG. 26 is a graph showing the relationship between floor vibration and the frequency of vibration of the normal mode of the floor.

A model for floor vibrations was tested to determine the optimum frequency of vibration of the normal mode, with data given in FIG. 26.

Shown here is an actual measured example of vibrations of a floor, where a gap (channel) was formed in a propagation path in an urban area, for an anti-vibration measure. As is clear from FIG. 26, the vibrations of less than 10 Hz are most numerous, and when the vibrations are increased with a lower frequency of vibration of the normal mode, as according to the prior art, the measurement is impaired. Such noise has conventionally been cut with a filter, but when cut with a filter the data of less than 10 Hz causes a distortion which renders the data unacceptable. The data of a brain magnetic field is obtained by measurement over a range of 1 to 300 Hz, but few Hz or less the measurement data contains much noise, and is thus not useful.

However, when the frequency of vibration of the normal mode is 10 Hz or greater, the level of noise is 10 ft or less, which enables the measurement of biomagnetic fields. Consequently, when the frequency of vibration of the normal mode is at least about 10 Hz or greater, preferably about 25 Hz or greater, and more preferably about 30 Hz or greater, a reduction in the vibrational noise may be expected, and accurate measurements are possible even with biomagnetic fields of less than about 10 Hz.

Figure 5:
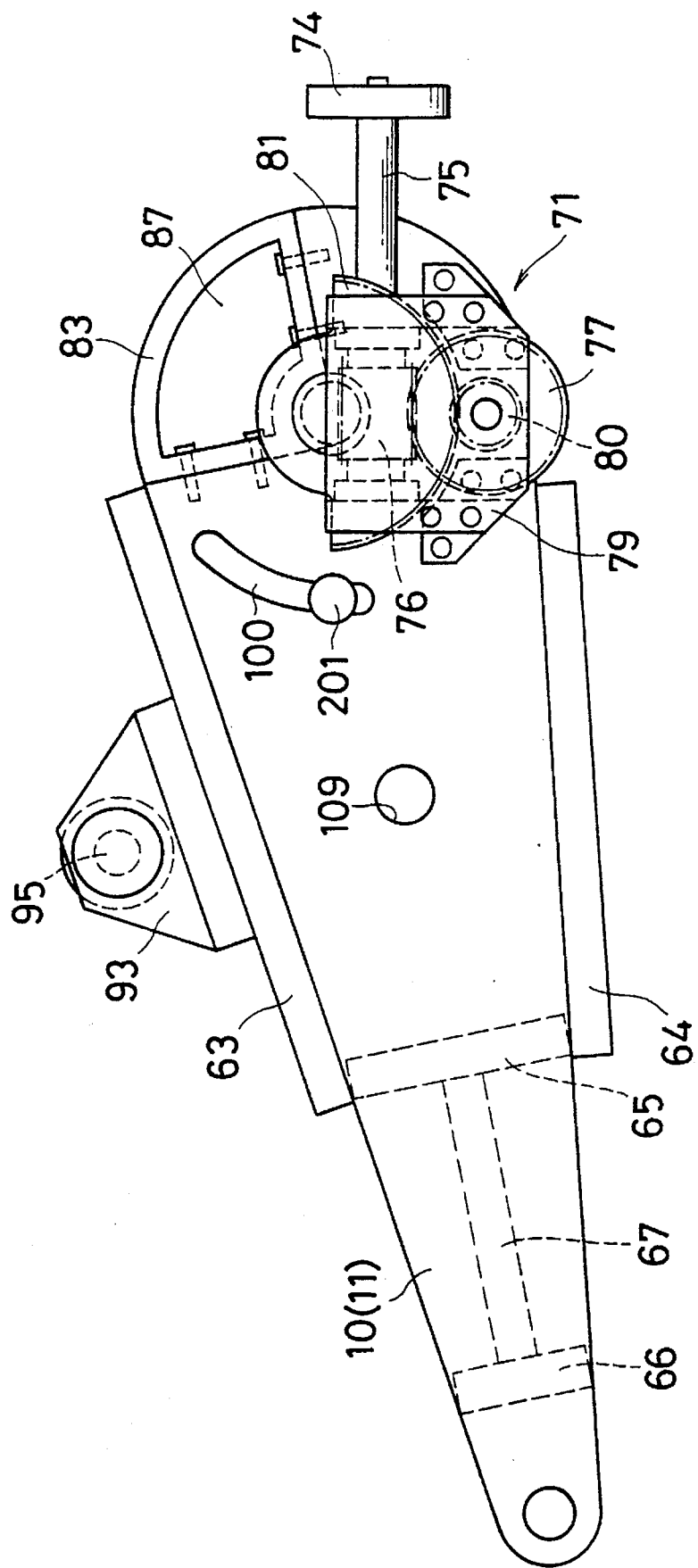
FIG. 5 is a side view of an arm according to the invention.
Figure 6:
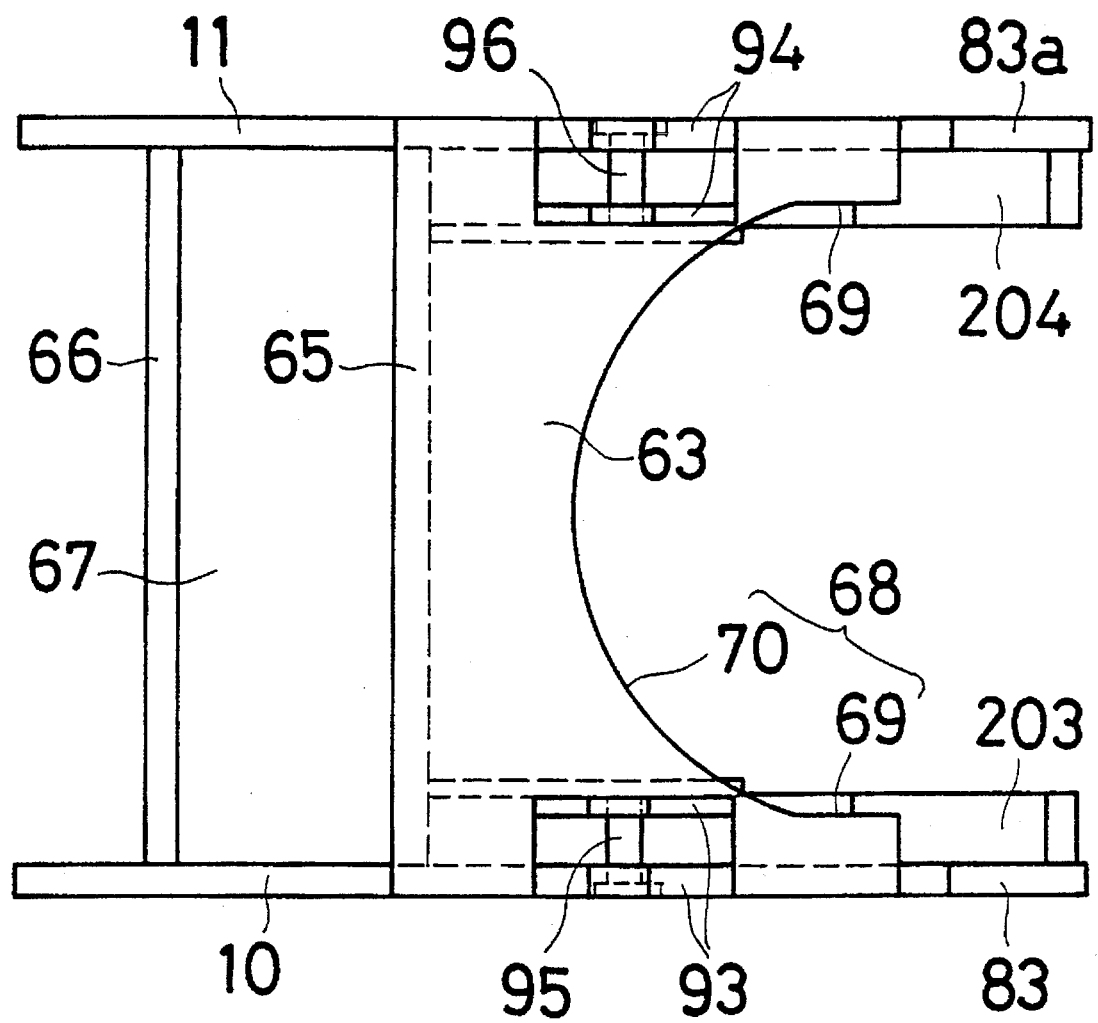
FIG. 6 is a plane view of arms and connecting members according to the invention.

FIG. 5 is a side view of the arms 10, 11, and FIG. 6 is a plane view of the arms 10, 11. This pair of arms 10, 11 are held together by vertically arranged connecting members 63, 64 which connect them, and this improves the rigidity of the arms 10, 11. These arms 10, 11 are also connected by longitudinal connecting members 65, 66 and a lateral connecting member 67 at the side of the brackets 41, 42 (on the left side in FIGS. 5 and 6), and this condition further improves the rigidity of the connecting members. The connecting member 63 has a curved notch 68 along the outer periphery of a supporting ring 60 of the magnetic measuring apparatus 5. The notch 68 has parallel guiding sections 69 and an arc section 70. Reinforcing pieces 203, 204 are also anchored to the arms 10, 11.

As mentioned above, since the pair of arms 10, 11, on the free distal ends of which is mounted the biomagnetic field-measuring apparatus 5, are connected together by the connecting members 63, 65, 66 between them to avoid displacement of the arms in the direction vertical to the arms, and thus the direction parallel to the pivoting axis of the biomagnetic field-measuring apparatus, the rigidity may be increased, and this further increases the frequency of vibration of the normal mode of the arms to prevent the adverse effect of noise.

Figure 7:
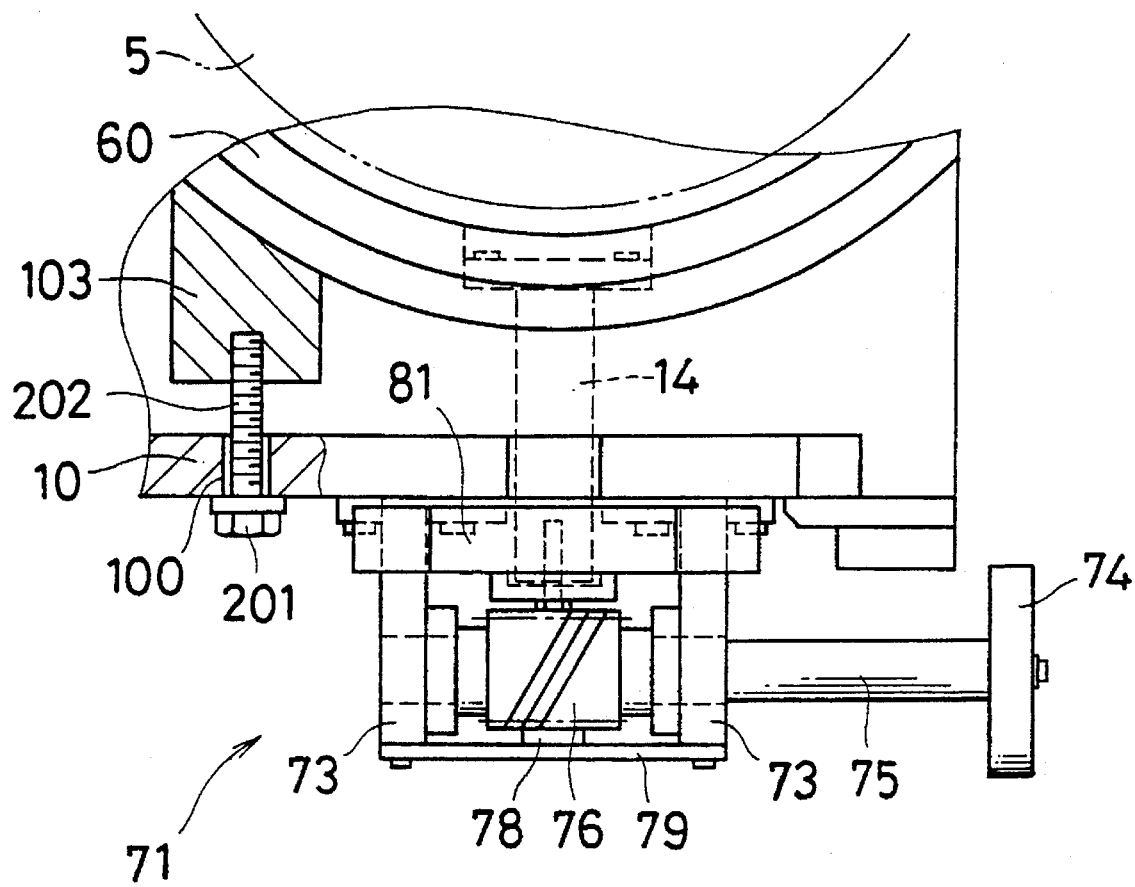
FIG. 7 is a plane view of pivoting means for pivoting magnetic field-measuring means according to the invention.
Figure 8:
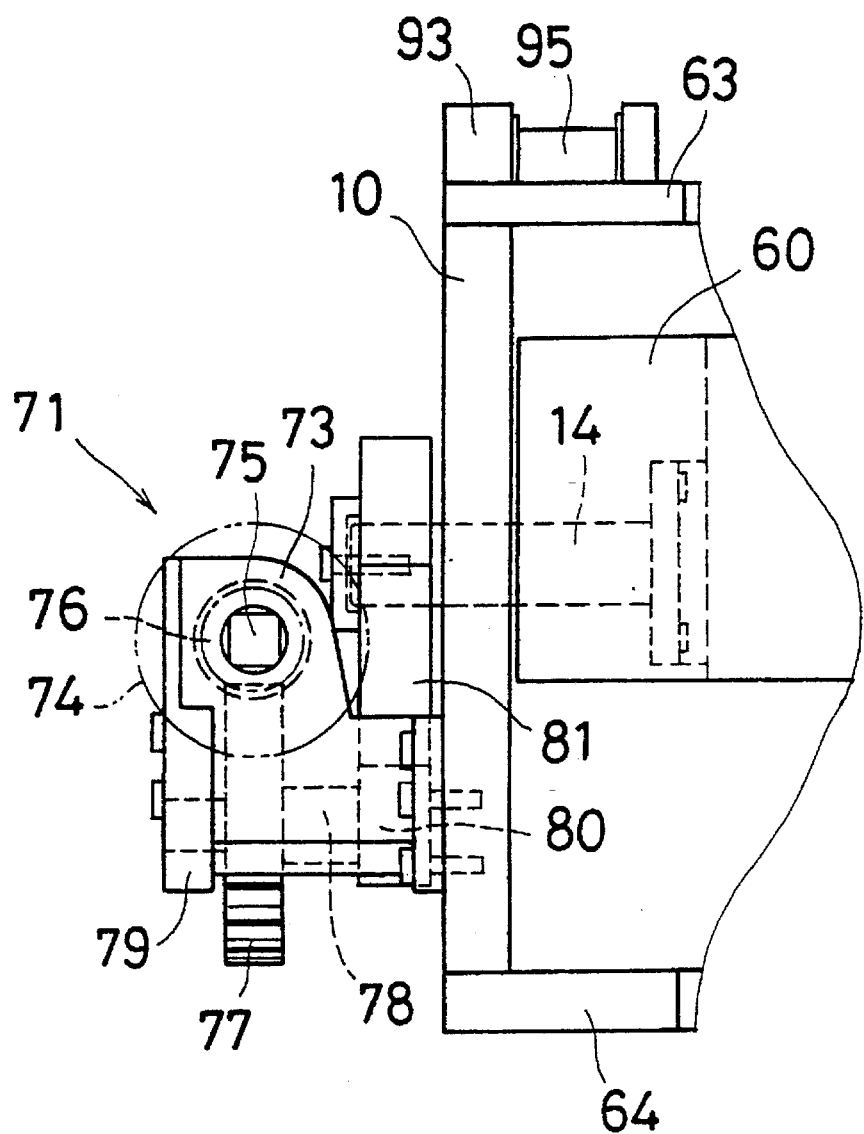
FIG. 8 is a front view of the pivoting means shown in FIG. 7.

FIG. 7 is a sectional view of the area near one of the arms 10. FIG. 8 is a front view of the pivoting means 71. As also shown in the following FIGS. 14 and 15, a supporting ring 60 is anchored to the magnetic field-measuring means 5, and a supporting shaft 14 mounted on the supporting ring 60 is driven by the pivoting means 71 which pivots around the horizontal axis for angular displacement to create a tilt. The bracket 73 mounted on the exterior of the one arm 10 is provided with a rotatable operating shaft 75 to which is anchored a handle 74. A worm 76 is anchored to this operating shaft 75. Below the worm 76 is situated an worm wheel 77 which is engaged therewith. The worm wheel 77 is anchored to a rotating shaft 78, and this shaft 78 is constructed between a supporting plate 79 and the arm 10 in a freely rotatable manner. A gear 80 is anchored to the rotating shaft 78, and engaged with the gear 80 is a sector gear 81 whose cross section is roughly semicircular. This sector gear 81 is anchored to the supporting shaft 14. Thus, upon rotating the handle 74, the worm 76, worm wheel 77, rotating shaft 78, gear 80 and sector gear 81 are rotated causing angular displacement of the supporting shaft 14, and in response to the displacement, the magnetic field-measuring means 5 is pivoted.

Figure 9:
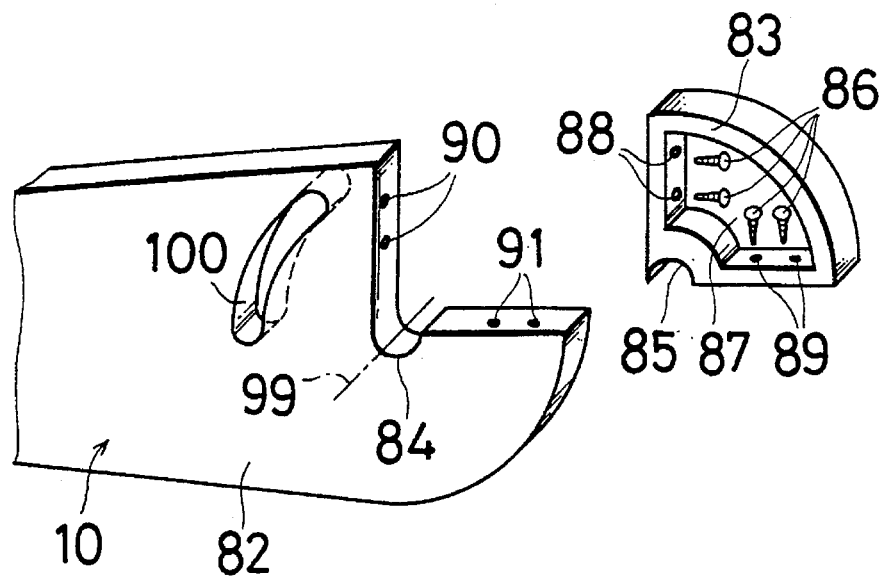
FIG. 9 is a schematic partial perspective view showing the free distal end section of an arm according to the invention.

FIG. 9 is a schematic view of the free distal end section of the arm 10. The arm 10 includes an arm body 82 and a mounting piece 83 on the top of the free distal end thereof, and the mounting piece 83 is detachable from the arm body 82. A depression 84 is formed in the arm body 82 in an arc covering about 180°. The mounting piece 83 has a depression 85 covering about 180°. The mounting piece 83 has a depression or an insertion hole 87 for attachment and bolts 86 are inserted into bolt insertion holes 88, 89, and threadedly engaged with screw holes 90, 91 formed in the end surface of the arm body 82, and this allows the supporting shaft 14 to be sandwiched between the upper and lower depressions 84, 85 for support. The other arm 11 is not provided with pivoting means 71, but it has a mounting piece with the same construction as the mounting piece 83, the supporting shaft 15 is mounted by being sandwiched vertically, and the mounting piece is indicated by 83a in FIG. 6.

According to the above-mentioned embodiment, the arms 10, 11 and magnetic field-measuring means 5 are anchored in a detachable manner by, for example, anchoring the mounting piece 83 at the top of the free distal end of the arm to the arm body in a removable manner to support the supporting shaft 14 of the magnetic field-measuring means 5, thereby allowing easy mounting and removal of the magnetic field-measuring means 5 at the free distal ends of the arms.

Brackets 93, 94 are anchored to the top surface of connecting member 63 almost directly above each arm 10, 11. Pins 95, 96 are anchored to the brackets 93, 94 and the ends of belts 97, 98 described later are connected to the pins and the arms are thus suspended so as to allow vertical motion.

An arcane guide hole 100 is formed in the arm 10, centered around the center line 99 of the depression 84. The shank 202 of a bolt 201 runs through the guide hole 100, as shown in FIG. 7. The shank 202, as shown in FIG. 7, is threadedly engaged with an attachment base 103 made of a non-magnetic material such as fiber-reinforced plastic or the like, which is anchored onto a supporting ring 60. With the magnetic field-measuring means 5 pivotable by pivoting means 71, the bolt 201 may be tightened to anchor the arm 10 and the supporting ring 60, and thus the measuring means 5. As a result, the vibration resistance is improved, and it is possible to increase the frequency of vibration of the normal mode to about 30 Hz or higher, as mentioned above. The other arm 11 has the same construction.

Figure 10:
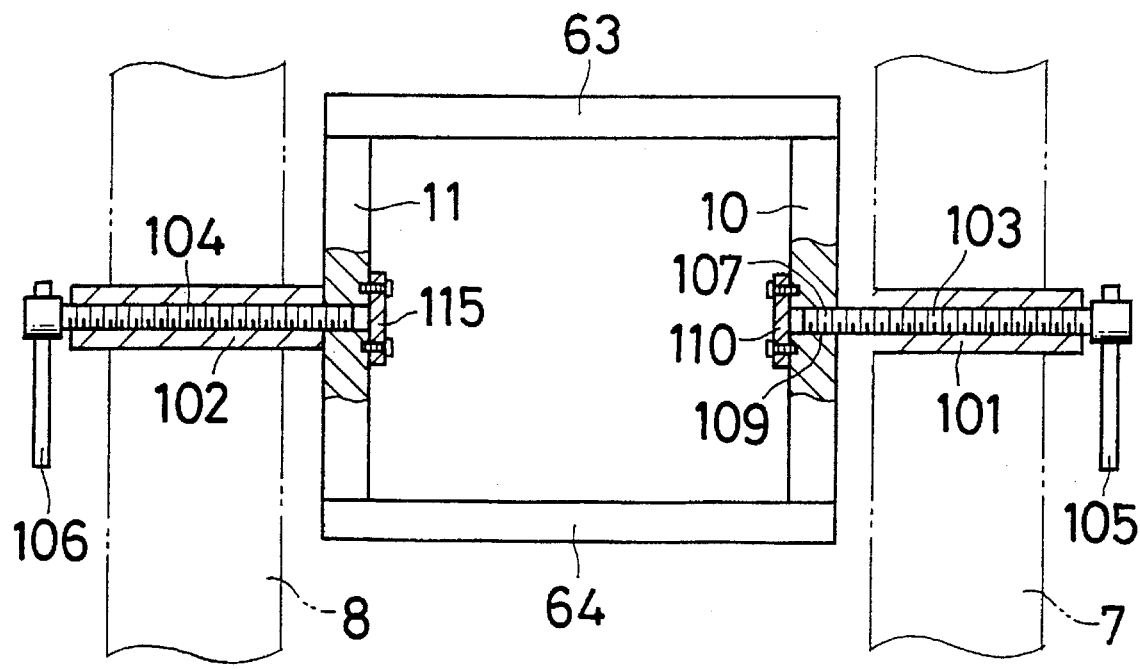
FIG. 10 is a schematic sectional view showing the state of an arm anchored to a supporting pillar according to the invention.
Figure 11:
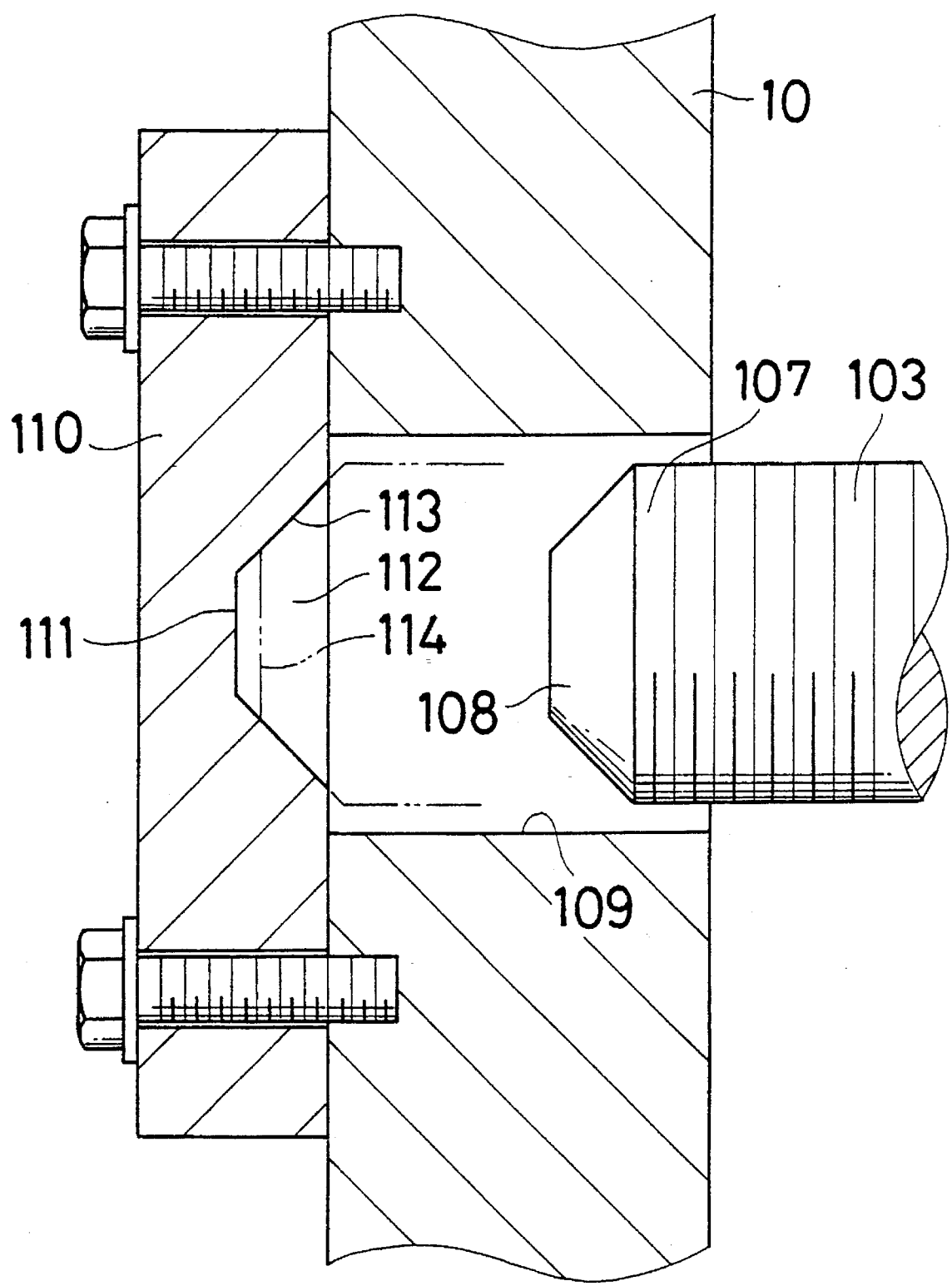
FIG. 11 is an enlarged sectional view showing the top section of a screw used to anchor a supporting frame and an arm according to the invention.

With the construction shown in FIG. 10, the arms 10, 11 are kept anchored to the supporting pillars 7, 8 during measurement. Cylinders 101, 102 are anchored to the supporting pillars 7, 8, and inside screws are tapped into the inner surface of the cylinders 101, 102. Screws 103, 104 are threadedly engaged with the cylinders 101, 102, and are rotatable by handles 105, 106. The top section 107 of the screw 103 is tapered as shown in FIG. 11 under magnification, and the shown embodiment has a truncated cone-shaped surface 108. An insertion hole 109 is formed through the arm 10 into which the top section 107 of the screw 103 is inserted. A holding member 110 is anchored to the surface of the arm 11 side of the arm 10. A depression 112 is formed in the holding member 110, whose inner diameter decreases toward the bottom 111 and whose inner surface 113 is sloped to match the truncated cone-shaped surface 108 of the screw 103, and as a result the truncated cone-shaped surface 108 of the top section 107 is fitted into the depression as indicated by the imaginary line 114, and the screw 103 and holding member 110 are held fast by the wedge action. The supporting pillar 7 and the arm 10 thus anchored. Another holding member 115 is anchored to the other arm 11, and the arm 11 is anchored to the supporting pillar 8 by the same construction. This construction also makes it possible to increase the frequency of vibration of the normal mode to 25 Hz or greater and thus avoid the adverse effect of noise.

Figure 12:
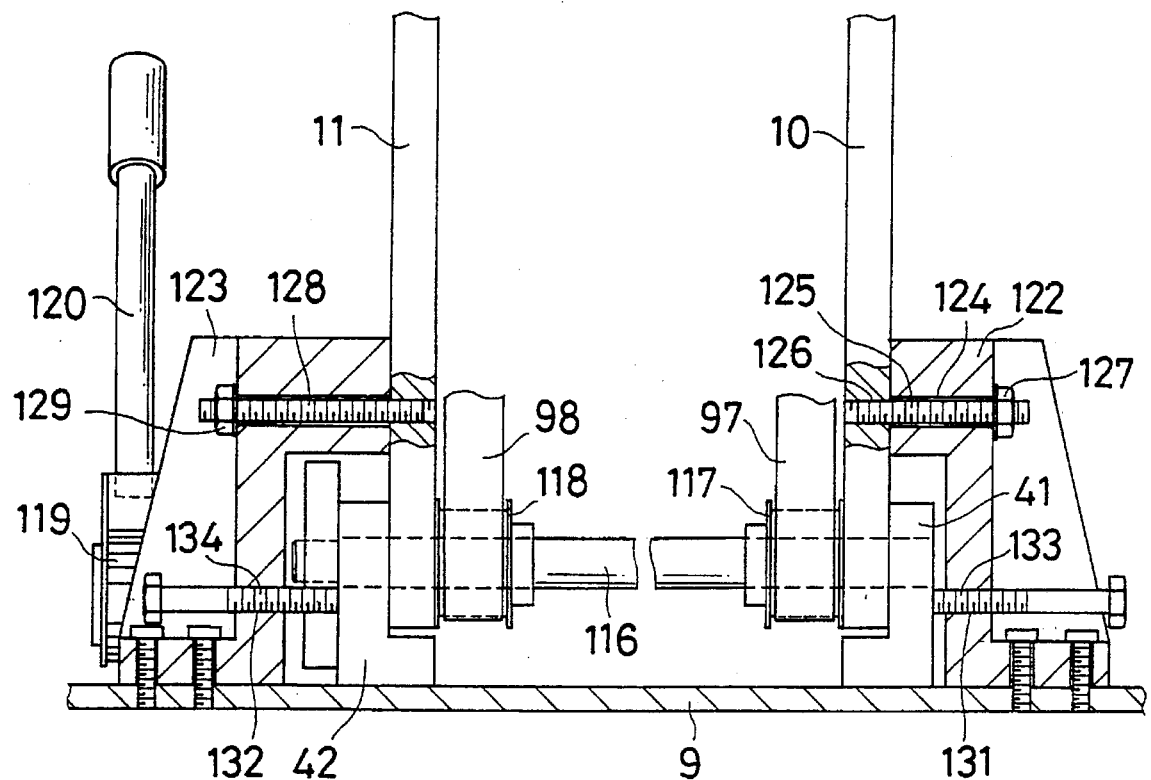
FIG. 12 is a horizontal sectional view showing the proximal end sections of arms according to the invention.

FIG. 12 is a horizontal sectional view of the proximal ends sections of the arms 10, 11. A shaft 116 which runs through the proximal ends of the arms 10, 11 is provided between the brackets 41, 42. The shaft 116 and the arms 10, 11 are mutually rotatable. Wind-up drums 117, 118 are anchored to the shaft 116, and they are capable of winding and unwinding belts 97, 98 with a winch 119. The winch 119 is operated by the reciprocating displacement of an operating lever 120. The belts 97, 98 are connected to the pins 95, 96 shown in FIGS. 5 and 6, via a pulley mounted on the ceiling as shown in FIG. 1. Thus, by the action of the winch 119, the belts 97, 98 suspending the arms 10, 11 are able to raise and lower the magnetic field-measuring means 5 mounted on their free distal ends. To anchor the proximal ends of the arms 10, 11 fast to the wall 9 of the magnetically shielded room, the brackets 122, 123 are also anchored to the wall 9.

Figure 13:
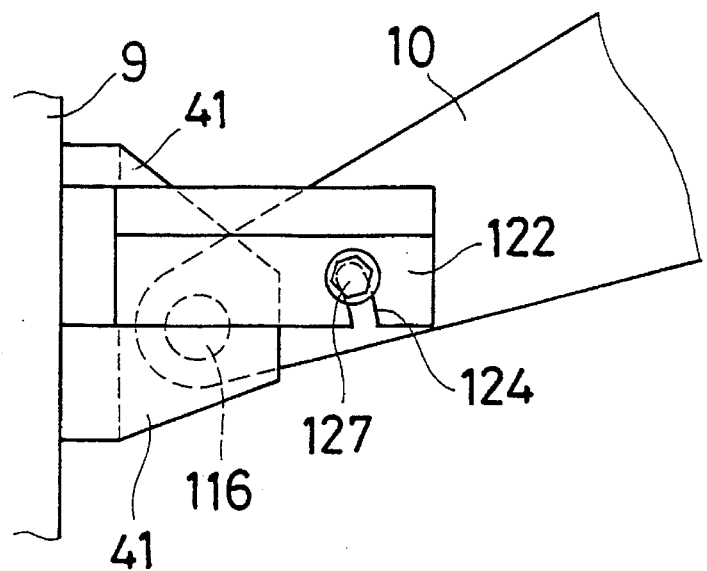
FIG. 13 is a side view of a bracket according to the invention which supports an arm against the wall of a shielded room.

FIG. 13 is a side view of the bracket 122. A notch 124 opening downward is formed in the bracket 122. This notch 124 forms an arc centered around the axis of the rotating shaft 116. One end of a stud bolt 125 lightly inserted into the notch 124 is anchored by being threadedly engaged with a screw hole 126 of the arm 10. A nut 127 is threadedly engaged with the screw 125, and when this nut 127 is tightened the arm 10 is anchored to the bracket 122 and thus the proximal end of the arm 10 may be anchored to the wall 9. A screw 128 and a nut 129 are provided on the other bracket 123 as well.

Bolts 133, 134 are threadedly engaged with the screw holes 131, 132 of the brackets 122, 123, and the bolts 133, 134 are tightened to strengthen the brackets 41, 42.

According to the above-mentioned embodiment, the bolts may be used to allow anchoring of the proximal ends of the pivotable arms onto the brackets 122, 123 which are anchored to the an anchoring spot such as the wall of a magnetically shielded room, and thus the undesirable vibration of the proximal ends of the arms may be prevented.

According to this construction, the supporting pillars 7, 8 are integrated with the arms 10, 11, the supporting pillars are anchored to the ceiling 46 and floor of the shielded room, and the arms 10, 11 are anchored to the wall 9, and this 3-way anchoring (ceiling, floor, wall) allows anchoring of the supporting means to allow utilization of the rigidity of the shielded room to increase the frequency of vibration of the normal mode of the supporting means and thus reduce the noise.

By securing a mechanical connection between the supporting means and the shielded room in the manner mentioned above, it is possible to minimize the amplitude of weak vibrations produced by the movement of the technician and accompanying persons, etc., by the mass of the shielded room.

Also, by securing a mechanical connection between the supporting means and the shielded room or other room, it is possible to use the mass of the room to minimize vibrations produced by the movement of the subject or physician.

Figure 14:
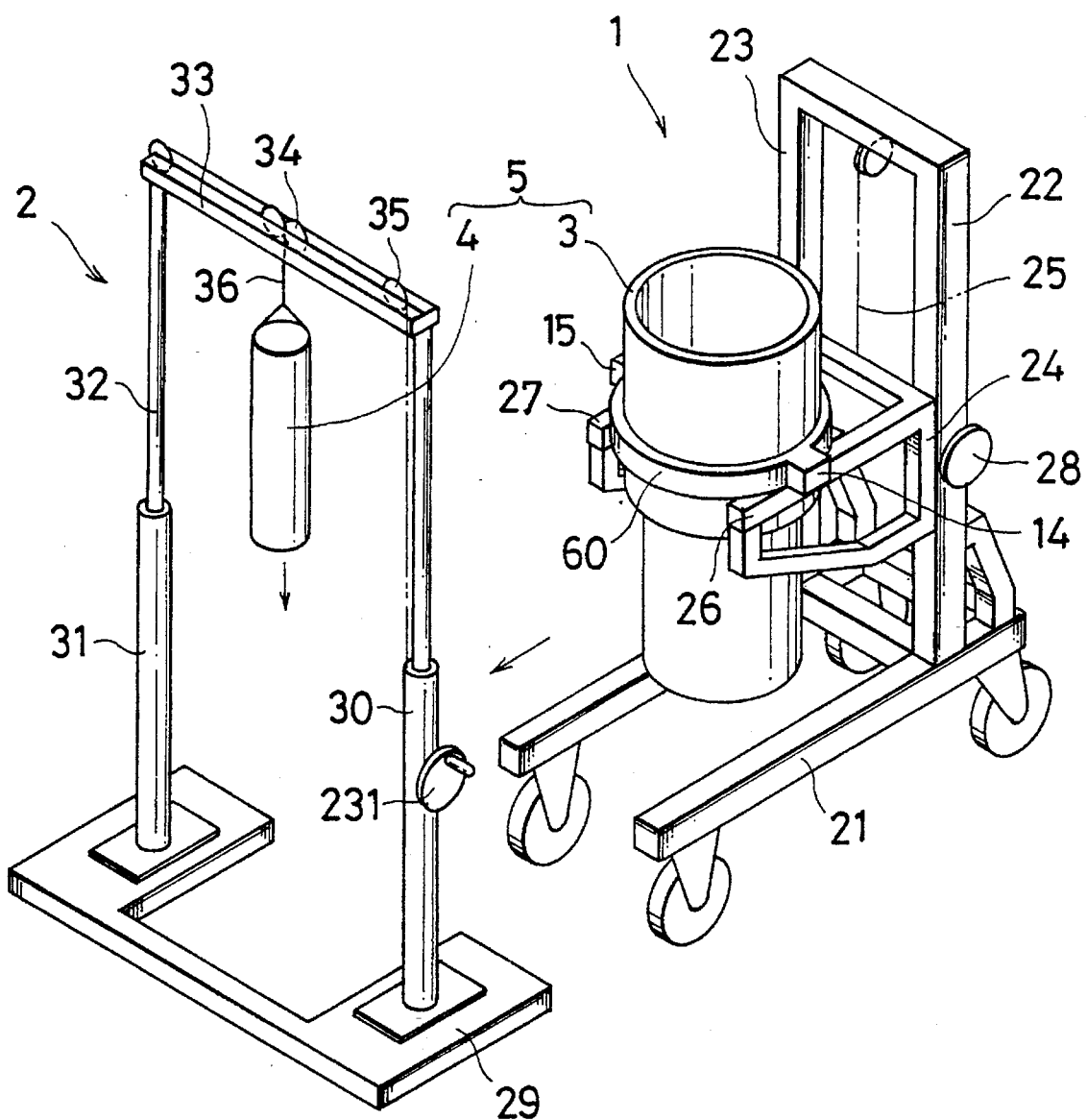
FIG. 14 is a schematic perspective view of a lifter and a suspending apparatus used for a biomagnetic field-measuring apparatus according to the invention.

In the biomagnetic field-measuring apparatus shown in the above-mentioned FIGS. 1 to 13, magnetic field-measuring means 5 is mounted on the arms 10, 11, with a lifter 1 and a suspending apparatus 2 shown in FIG. 14.

Figure 15:
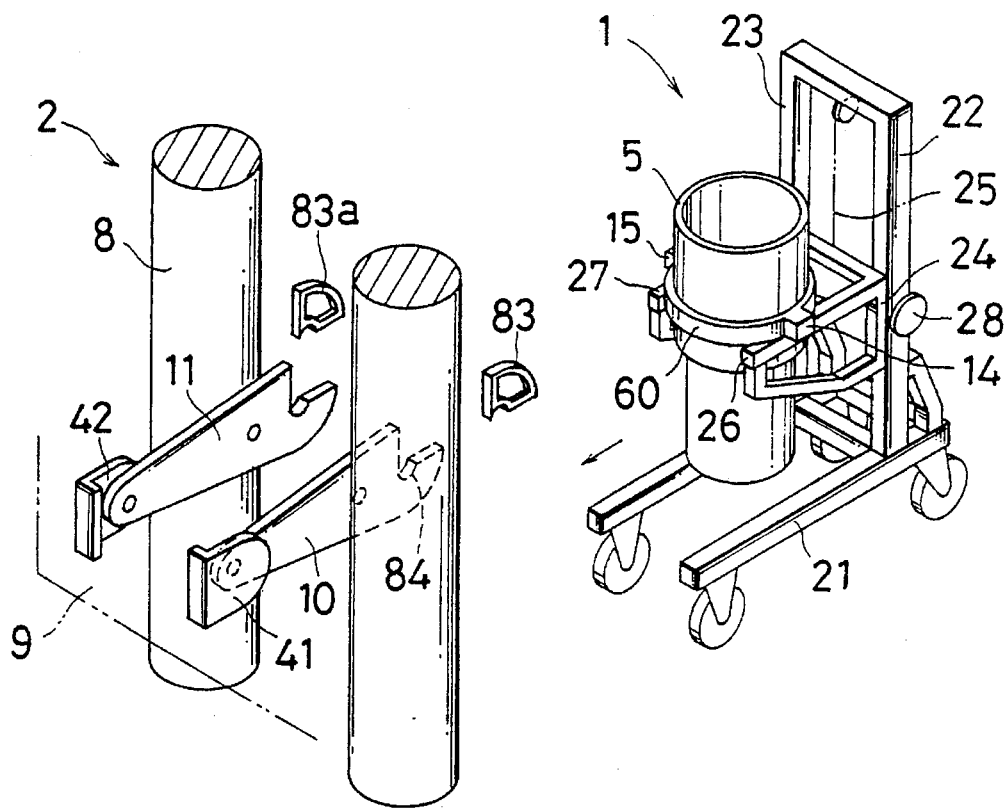
FIG. 15 is a schematic perspective view showing the assembly of a biomagnetic field-measuring apparatus according to the invention using a lifter and a suspending apparatus.

A cryogenic vessel 3 of the biomagnetic field-measuring apparatus may be moved by the lifter 1 for raising and lowering of its position, and a SQUID type fluxmeter 4 may be accurately received and mounted in the vessel 3 by the suspending apparatus 2. The magnetic field-measuring means 5 with the fluxmeter 4 received and mounted in the vessel 3 in this manner is moved by the lifter 1 as shown in FIG. 15, and between the pair of supporting pillars 7, 8 of the double housing type supporter 43, supporting shafts 14, 15 mounted on the vessel 3 are fitted into the shaft-bearing depressions 84, 85 of the pair of arms 10, 11 mounted on the wall 9 of the magnetically shielded room in a pivotable manner around the horizontal axis, to thus mount the vessel 3, and thus the magnetic field-measuring means 5, in a pivotable manner around the horizontal axis, after which the mounting pieces 83, 83a are anchored to mount the magnetic field-measuring means 5 on the arms 10, 11.

Figure 16:
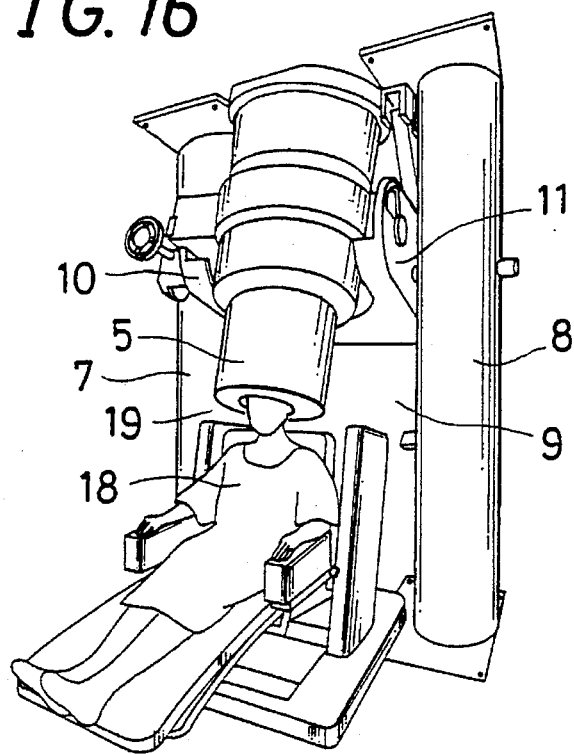
FIG. 16 is a schematic perspective view showing the state of measuring a brain magnetic field using a biomagnetic field-measuring apparatus according to the invention.

The lower side of the magnetic field-measuring means 5 is placed over the head 19 of a subject 18 as shown in FIG. 16, to allow high-precision measurement of the strength of a weak magnetic field generated from the body, for example the brain, of the subject 18.

The lifter 1 basically comprises a pair of supporting pillars 22, 23 built on a truck 21, and the position of a support 24 guided by these supporting pillars 22, 23 may be moved up and down by a cable 25. A pail of horizontally extending arms 26, 27 which are loaded with the vessel 3 are provided on the support 24, and the position of the arms 26, 27 can be adjusted in the direction perpendicular to the supporting pillars 22, 23 (in FIG. 15, roughly in left-right direction, or in the left-right width direction) by rotating a handle 28.

The suspending apparatus 2 basically comprises a double housing type supporting frame 32 on a base 29, and a pair of supporting pillars 30, 31 of the supporting frame 32 are built on the base 29. A cable 36 is wound around a first pulley 34 mounted on the upper connecting member 33 at the top of the supporting frame 32 and a second pulley 35 mounted near the top of one supporting pillar 30, and the cable 36 is wound/unwound by wind-up means 231 mounted on the supporting pillar 30, thus allowing the SQUID type fluxmeter 4 suspended from one end of the cable 36 to be smoothly raised and lowered.

The biomagnetic field-measuring apparatus, lifter 1, suspending apparatus 2, etc. according to the invention are made of a non-magnetic material such as aluminum, copper, stainless steel, synthetic resin, fiber-reinforced plastic, rubber, or the like.

Figure 17:
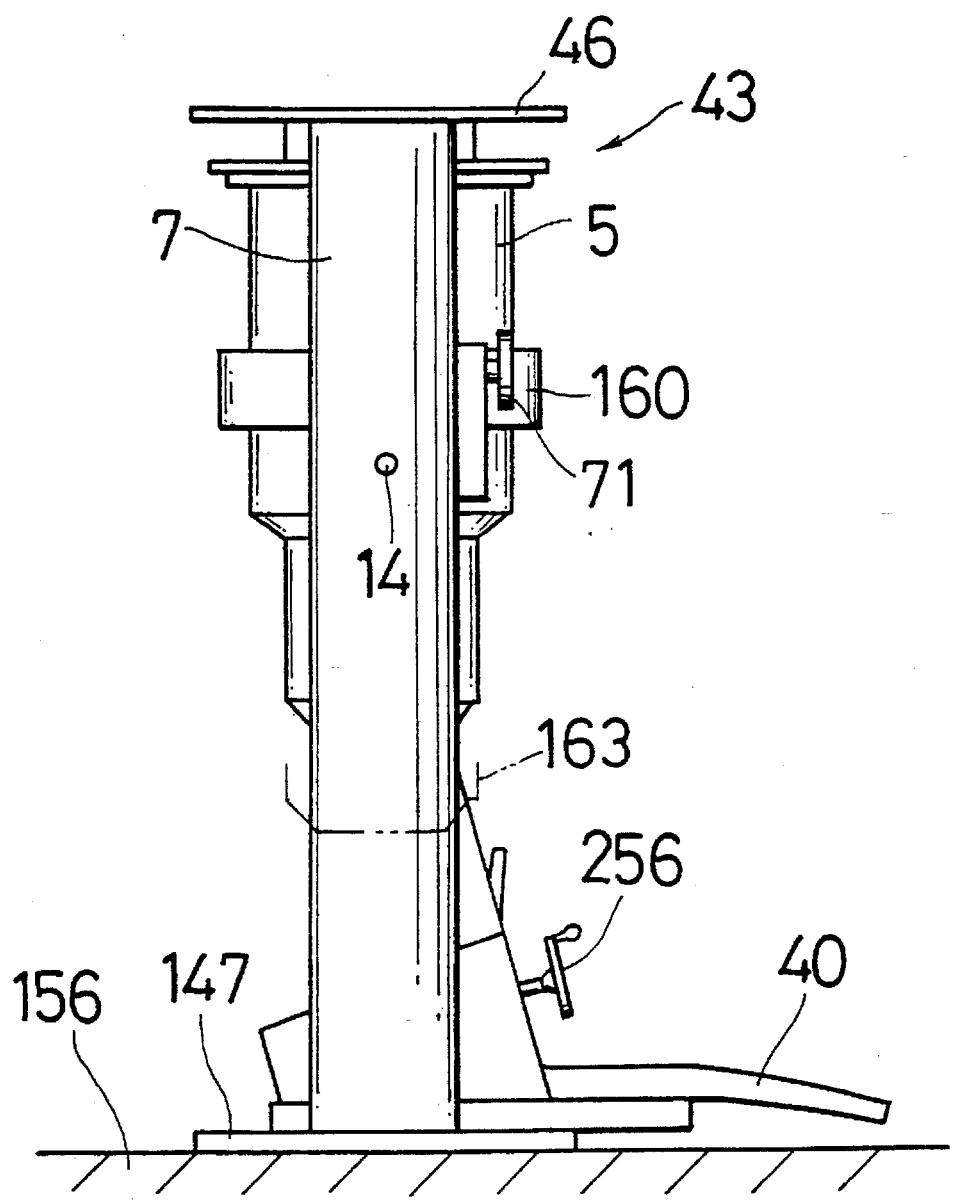
FIG. 17 is a side view of a biomagnetic field-measuring apparatus according to another embodiment of the invention.
Figure 18:
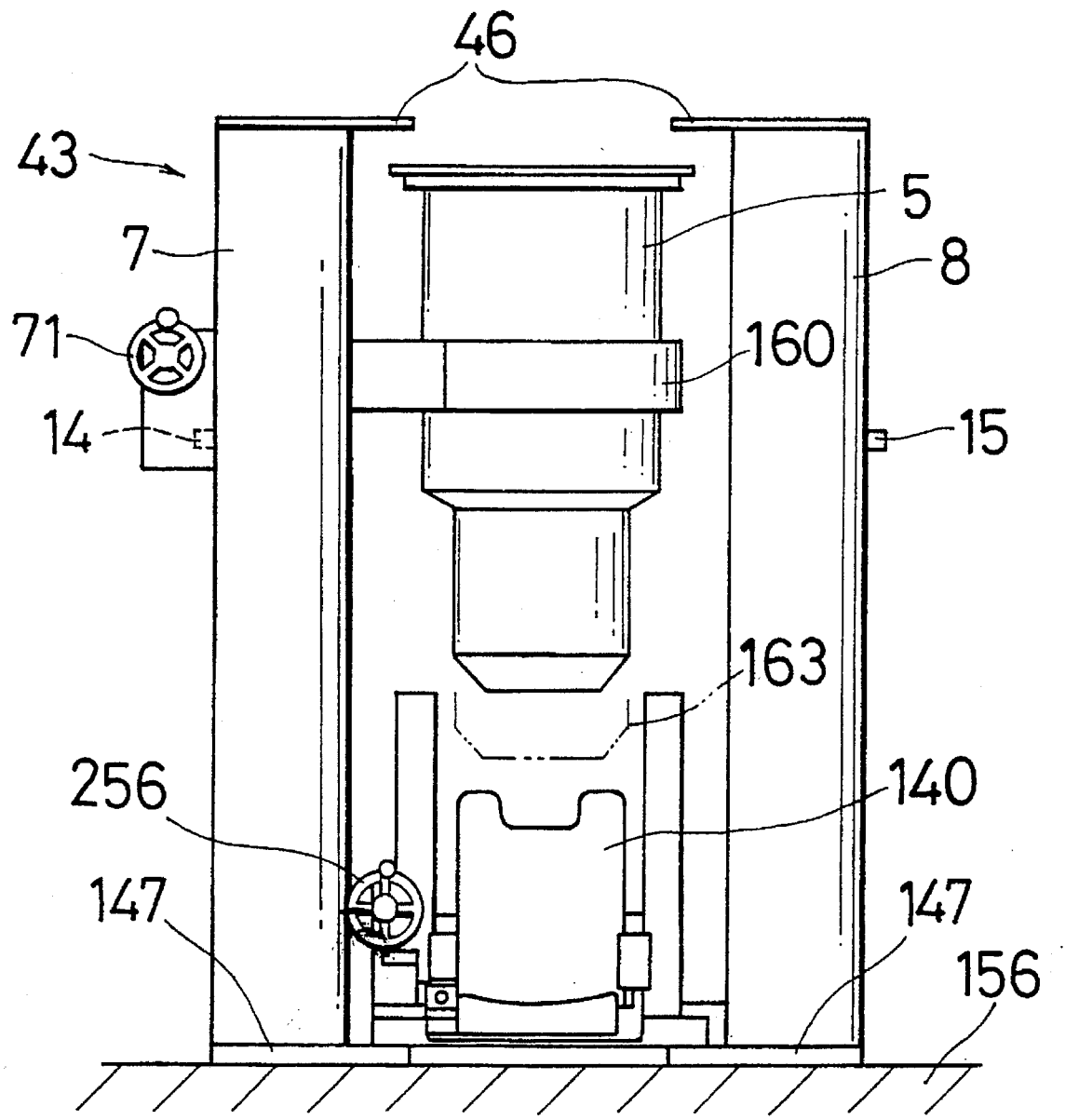
FIG. 18 is a front view of the biomagnetic field-measuring apparatus shown in FIG. 17.

FIGS. 17 and 18 show another embodiment of a biomagnetic field-measuring apparatus according to the invention.

For the magnetic field-measuring means 5, a base 147 is anchored to the floor 156 of a magnetically shielded room, a pair of supporting pillars 7, 8 are mounted on the base 147, and the tops of the supporting pillars 7, 8 are anchored to a ceiling board 46. The double housing type support 43 is thus composed of the pair of supporting pillars 7, 8 and the ceiling board 46. A support ring 60 is anchored to the magnetic field-measuring means 5, and a pair of supporting shafts 14, 15 with the axes in a horizontal line are anchored to this support ring 60. The supporting shafts 14, 15 are supported at the measuring position by the supporting pillars 7, 8, and are pivoted by angular displacement around the horizontal axes to allow tilting motion. Thus, by having no mechanism on the supporting pillars 7, 8 for raising and lowering the magnetic field-measuring means 5, the rigidity of the supporting pillars 7, 8 is increased and as mentioned above the frequency of vibration of the normal mode of the magnetic field-measuring means 5 may be 25 Hz or greater, and thus the amplitude may be reduced and noise contamination prevented. Pivoting means 71 is provided to pivot the magnetic field-measuring means 5.

Figure 19:
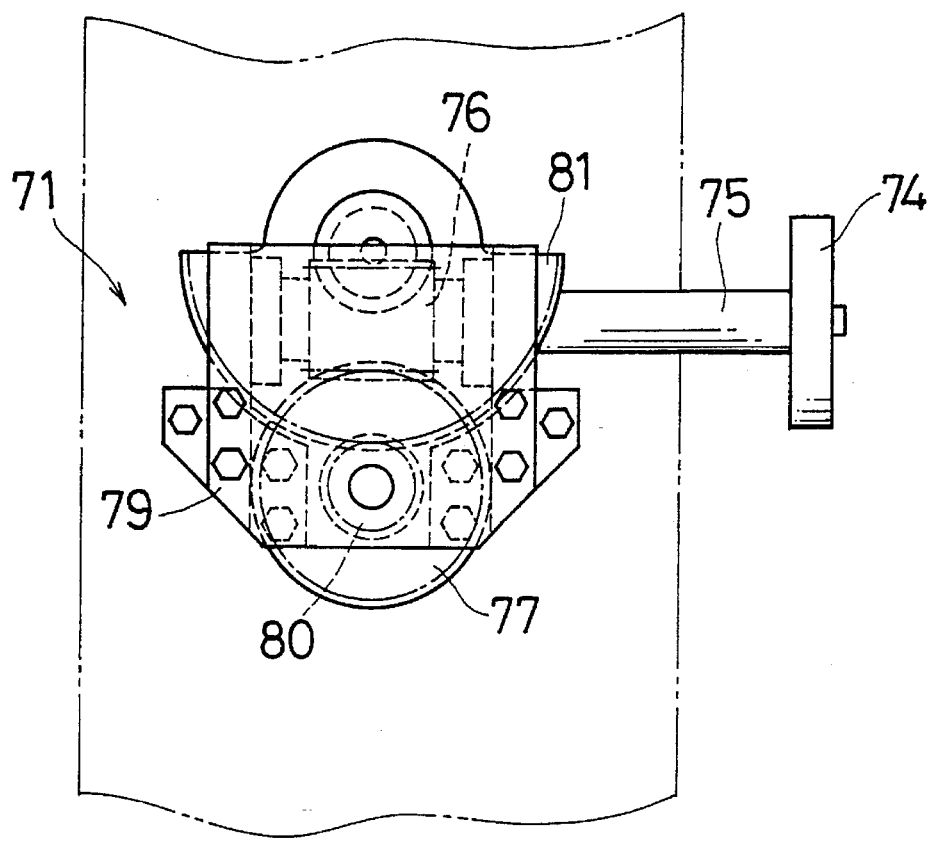
FIG. 19 is a side view of pivoting means for pivoting a magnetic field-measuring apparatus according to the invention.
Figure 20:
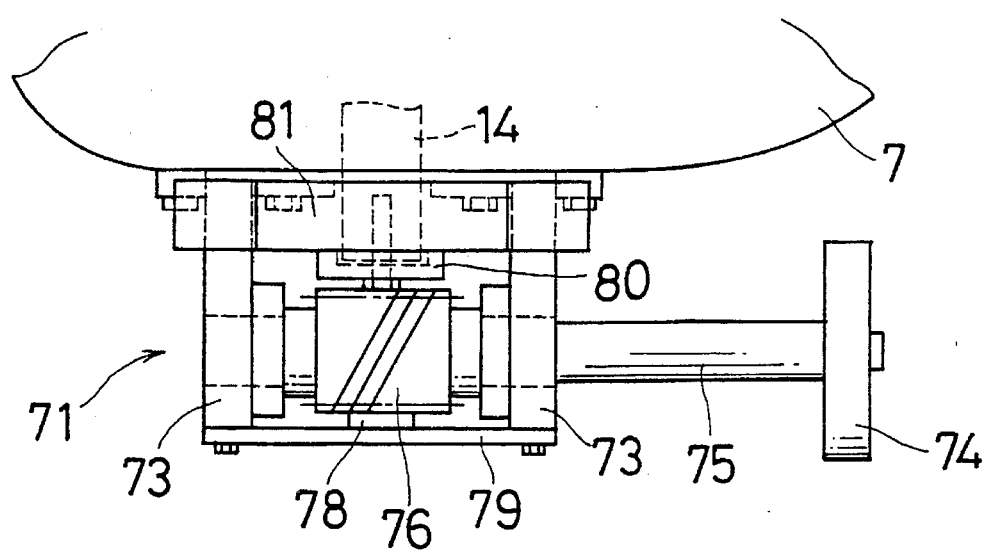
FIG. 20 is a plane view of the pivoting means shown in FIG. 19.
Figure 21:
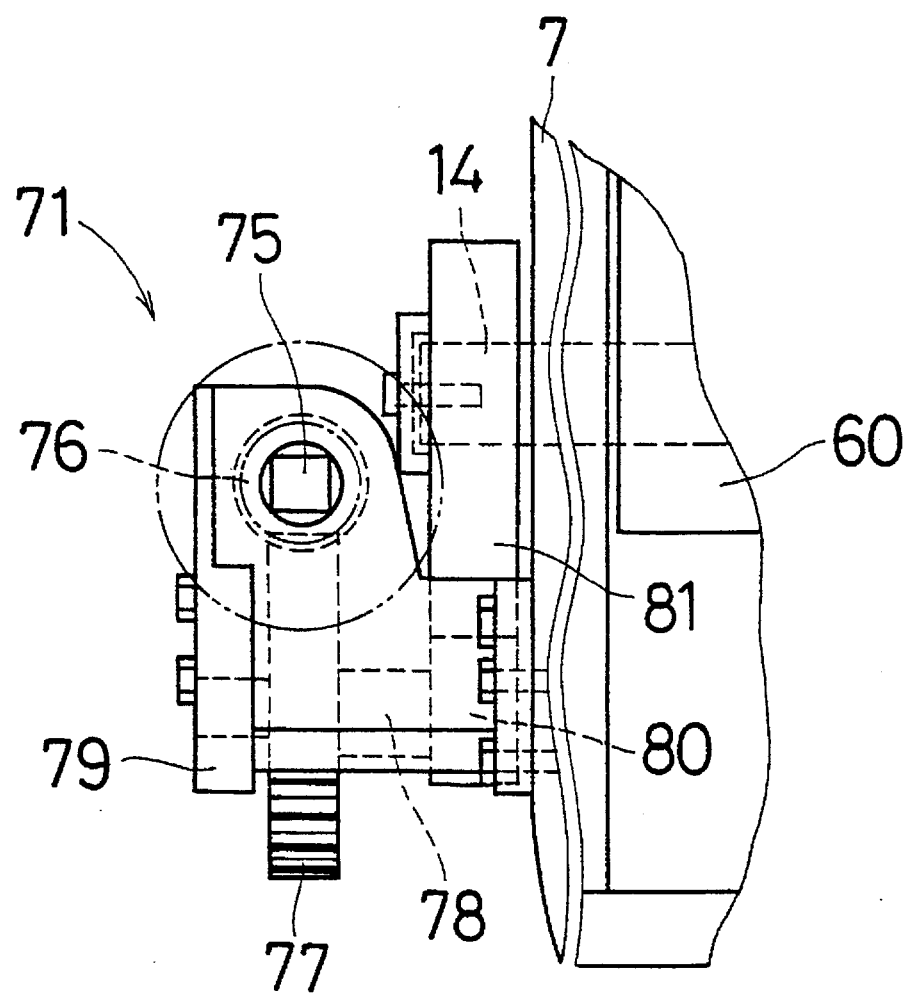
FIG. 21 is a front view of the pivoting means shown in FIG. 19.

FIG. 18 is a side view of the pivoting means 71. FIG. 19 is a plane view of the pivoting means 71. FIG. 20 is a front view of the same pivoting means 71. Since the pivoting means 71 is substantially identical to the means explained with reference to FIGS. 7 and 8, the following is a simplified description of its construction for FIGS. 18 to 21. An operating shaft 75 to which a handle 74 is anchored is mounted in a rotatable manner on the bracket 73 mounted on the outside of one supporting pillar 7. A worm 76 is anchored to this operating shaft 75. A worm wheel 77 placed below the worm 76 engages therewith. The worm wheel 77 is anchored to a rotating shaft 78, and the shaft 78 is mounted between a supporting board 79 and the arm 10 in a freely rotatable manner. A gear 80 is anchored to the rotating shaft 78, and the gear 80 engages with a sector gear 81 whose cross section is roughly semicircular. This sector gear 81 is anchored to the supporting shaft 14. Thus, upon rotating the handle 74, the worm 76, worm wheel 77, rotating shaft 78, gear 80 and sector gear 81 are rotated causing angular displacement of the supporting shaft 14, and in response to the displacement the magnetic field-measuring means 5 is pivoted.

According to the embodiment described above, the magnetic field-measuring means 5 is set on the double housing type support 43 so as to allow angular displacement, and therefore the frequency of vibration of the normal mode may be set to, for example, about 25 Hz or greater, to lower the amplitude of its resonance frequency and thus prevent noise contamination.

Figure 22:
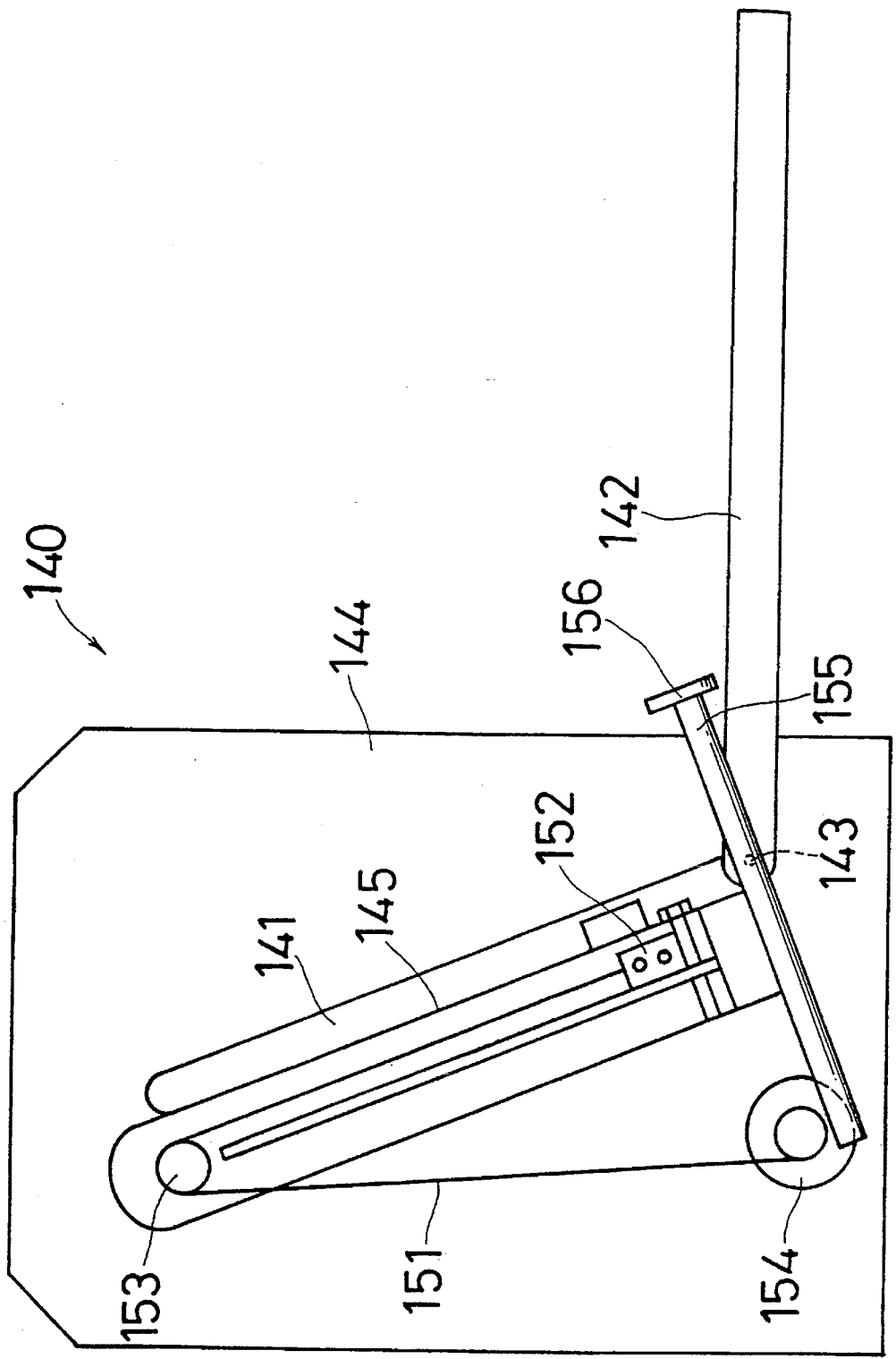
FIG. 22 is a schematic sectional view of a bed according to the invention.
Figure 23:
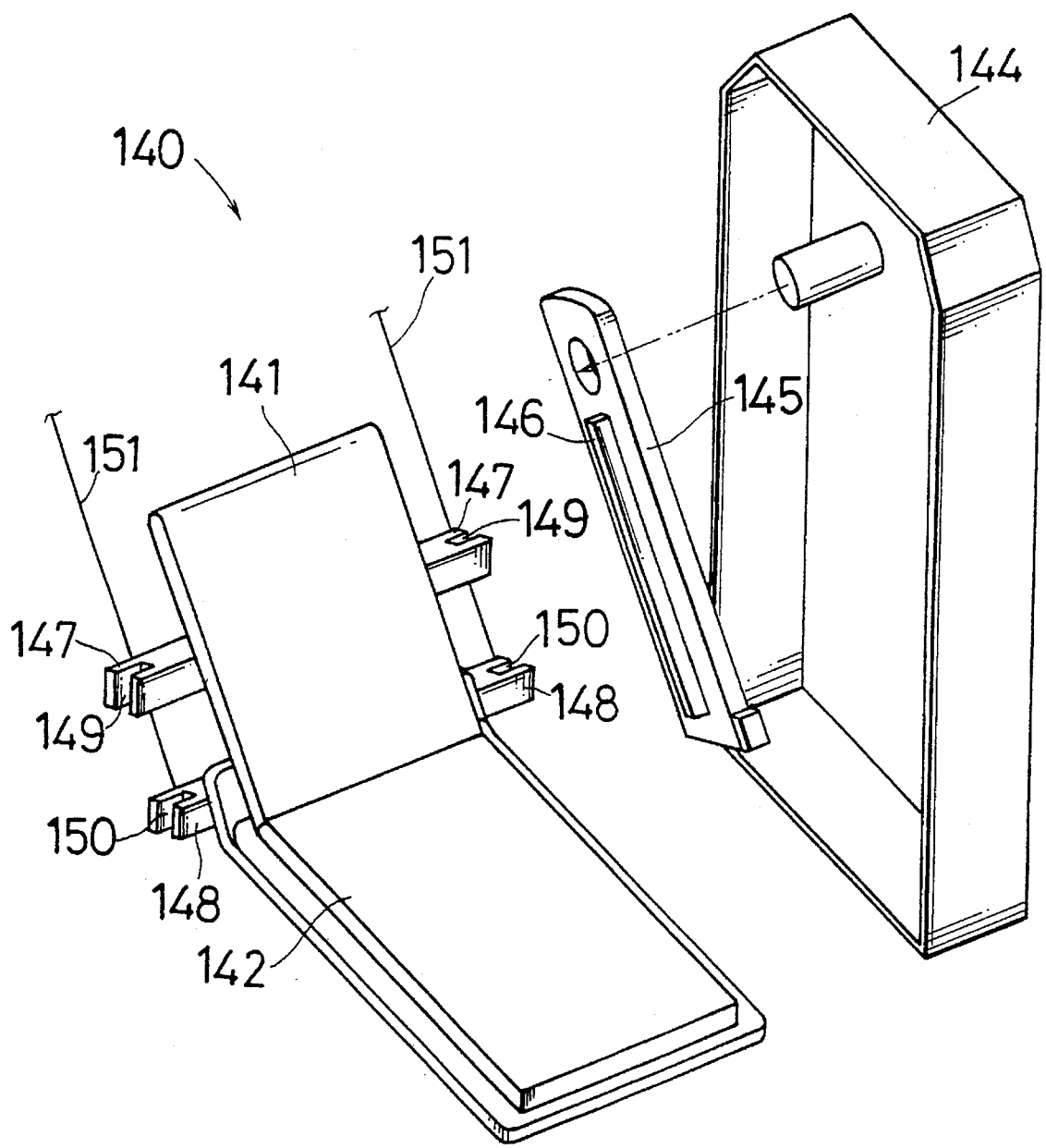
FIG. 23 is an enlarged perspective view of a part of the bed shown in FIG. 22.

FIG. 22 is a schematic view showing a human subject lying on a bed 140, and FIG. 23 is a partial perspective view thereof. The backrest section 141 and lying section 142 of the bed 140 are constructed so as to allow their angular displacement around a pin 143 with a horizontal axis line so that they may be anchored by any set angle. A holder 144 is provided on both the left and right sides of the backrest section 141 and lying section 142. The holder 144 is anchored to the floor 156 of the magnetically shielded room, or is constructed so as to be movable. A guiding rail 145 is anchored to the holder 144. A guiding protrusion 146 is formed on the guiding rail 145. The guiding protrusion 146 inclines upward from the lying section 142 to the backrest section 141. Guiding pieces 147, 148 are anchored to the lying section 142. The guiding pieces 147, 148 have respective guiding grooves 149, 150, and the guiding pro,fusion 146 fits into the guiding grooves 149, 150. Thus, the position of the lying section 142 may be moved along the guiding protrusion 146 of the guiding rail 145. The end of the cable 151 is anchored onto the backrest section 141 by a mounting piece 152.

A pulley 153 is provided on the holder 144. The cable 151 is wound around the pulley 153, and it is wound or unwound by a winch 154. The winch 154 may be operated by rotating an operating rod 155 with a handle 256. By winding the cable 151 with the winch 154, it is possible to raise and lower the backrest section 141 and lying section 142 along the guiding rail 145 while maintaining the angle between them. It may also be constructed so that the angle of the guiding rail 145 may be changed.

Figure 24:
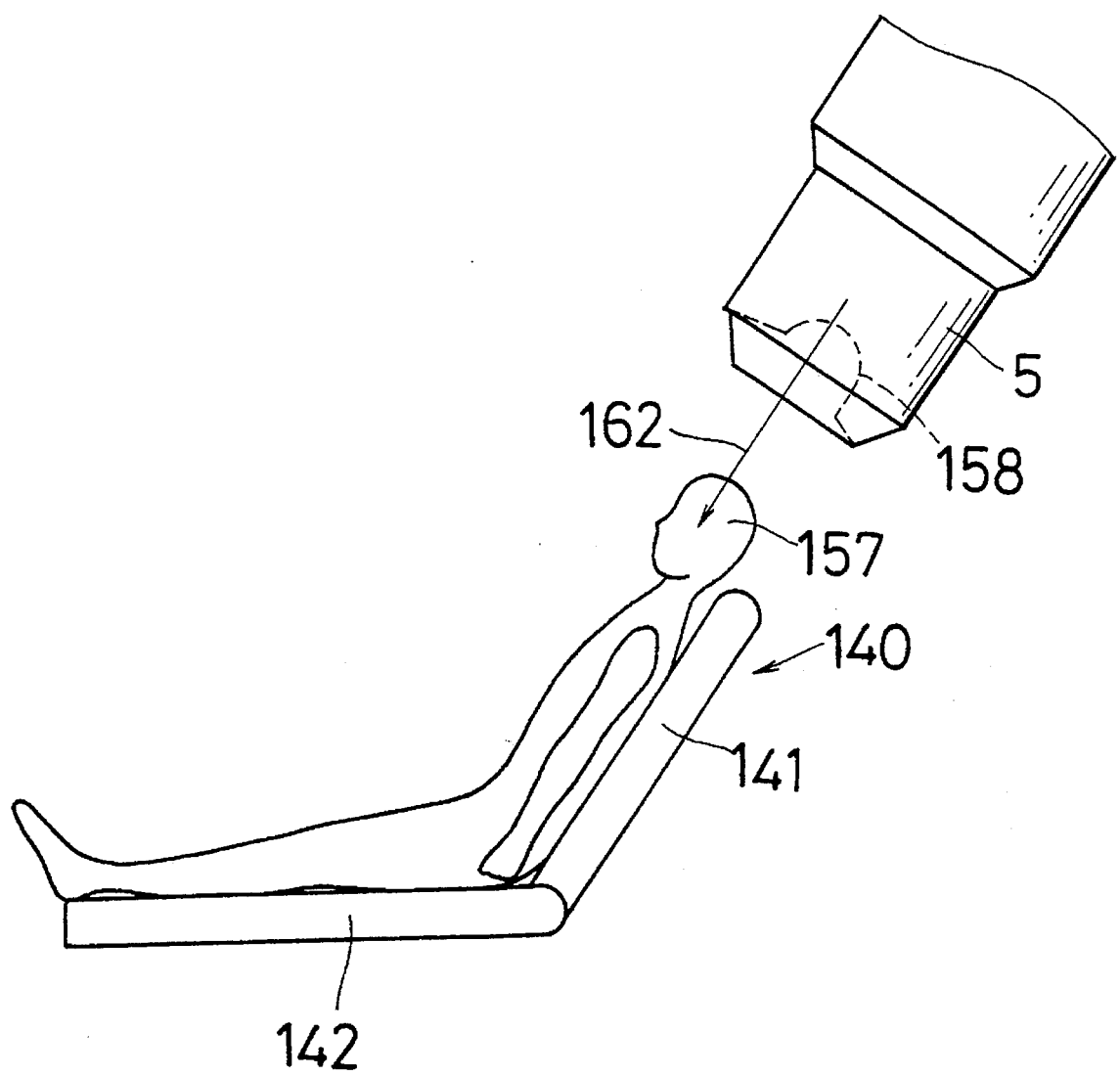
FIG. 24 is a schematic view showing the state wherein a subject lying on the bed shown in FIG. 22 is measured using a brain magnetic field-measuring apparatus according to the invention.

Referring to FIG. 24, the head of a subject 157 may be fitted in the measuring hollow 158 of the magnetic-field measuring means 5 to allow measurement of the biomagnetic field of the brain. The backrest section 141 and lying section 142 of the bed 140 are moved up and down along the guiding rail 145 as shown by the arrow 162, thus allowing the subject 157 to be moved along the axis of the pivoted and set magnetic field-measuring means 5 for satisfactory measurement.

According to this embodiment, the body of the subject lying on the bed may be moved up and down by the movement of the bed to align the position of the brain or other part of the subject to be measured for a magnetic field, with the magnetic field-measuring means. Hence, there is no need to move the magnetic field-measuring means up and down for the measurement, and consequently the rigidity of the magnetic field-measuring means is increased, making it possible to raise the frequency of vibration of the normal mode and lower the amplitude.

The lifter 1 and suspending apparatus 2 shown in FIG. 14 are used for the mounting and removal of the magnetic field-measuring means 5 from the double housing type support 43. The supporting shafts 14, 15 which are mounted on the magnetic field-measuring means 5 via the supporting ring 60 may also be placed on the support 43 as shown by the imaginary line 163, at a maintenance position below the magnetic field-measuring position shown by the solid lines in FIGS. 17 and 18, supporting the magnetic field-measuring means 5 at this position 163 by the supporting pillars 7, 8.

Figure 25:
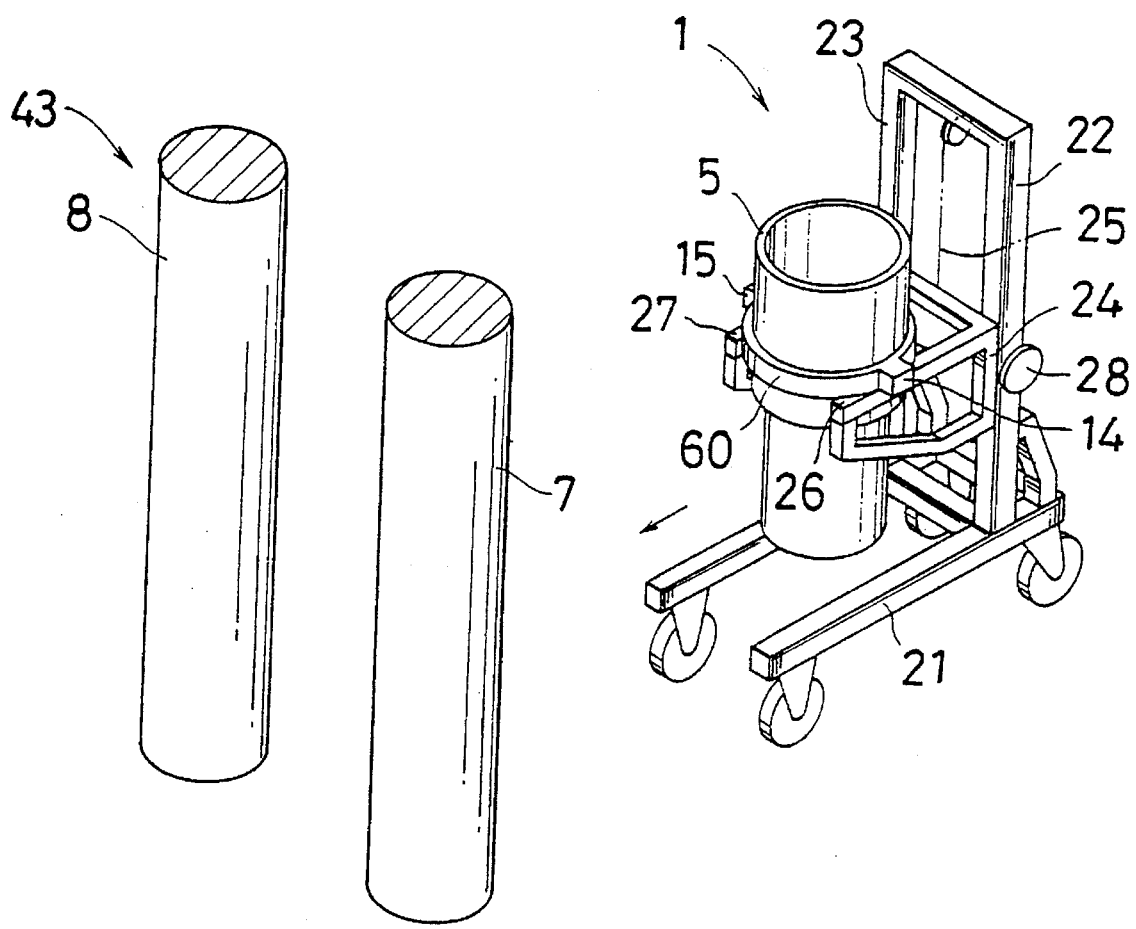
FIG. 25 is a schematic perspective view showing the assembly of a biomagnetic field-measuring apparatus according to the invention.

According to this embodiment, the magnetic field-measuring means 5 with the fluxmeter 4 mounted inside the vessel 3 is moved by the lifter 1 as shown in FIG. 25, and the supporting shafts 14, 15 are fitted into the pair of supporting pillars 7, 8 making up the double housing type support 43 to allow the magnetic field-measuring means 5 to pivot around the horizontal axis at a maintenance position or at a measuring position.

Figure 27:
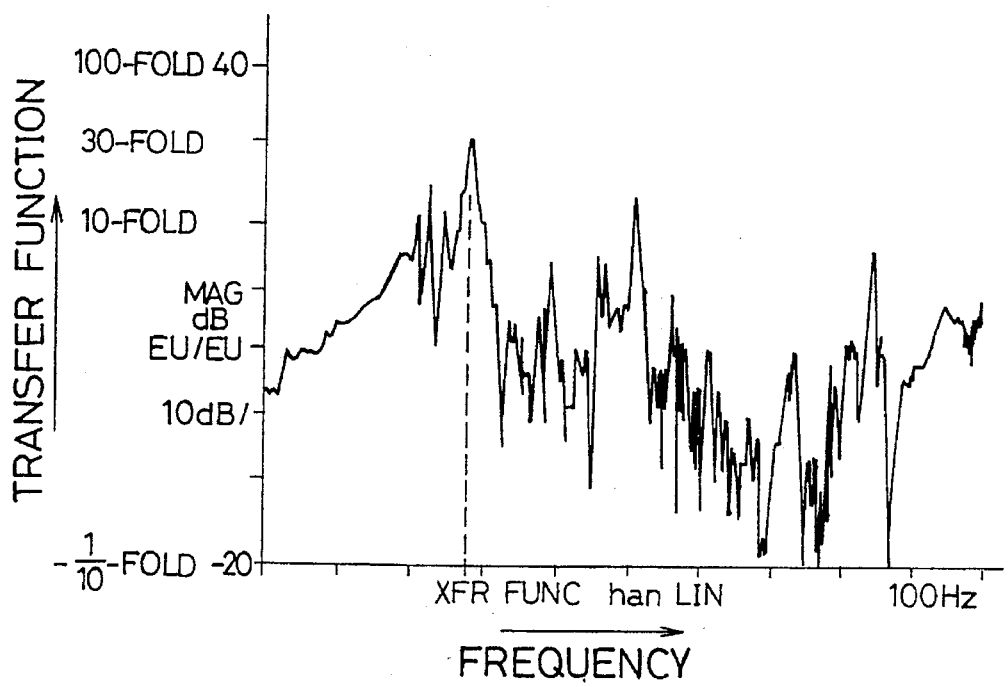
FIG. 27 is a graph showing the frequency of vibration of the normal mode of supporting means according to the invention.

FIG. 27 shows the frequency of vibration of the normal mode of supporting means according to the invention. The horizontal axis shows frequency, and the vertical axis the amplification of vibration at the supporting ring which supports the magnetic field-measuring assembly with the floor as reference. That is, the amplification of vibration of the support/floor is 0 dB (1x) at 0 Hz and about; 30 dB (30x) at 27.75 Hz. The frequency of vibration of the normal mode of the supporting means is about 25 Hz. The amplitude of the ring at this frequency of vibration of the normal mode is kept to 0.4 µm or less (one-directional amplitude). For example, compared to a case where the frequency of vibration of the normal mode is 2.5 Hz, an amplitude of 2.5 Hz may be expected to increase about 100-fold.

Figure 28:
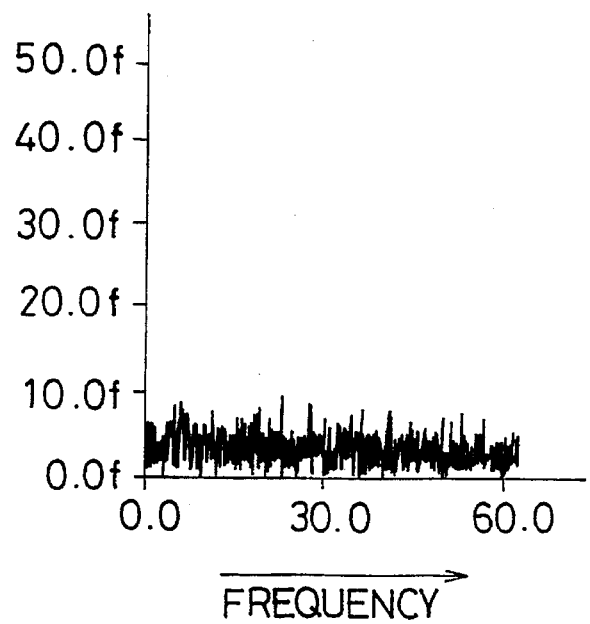
FIG. 28 is a graph showing the results of measurement of noise with a brain magnetic field-measuring apparatus according to the invention.
Figure 29:
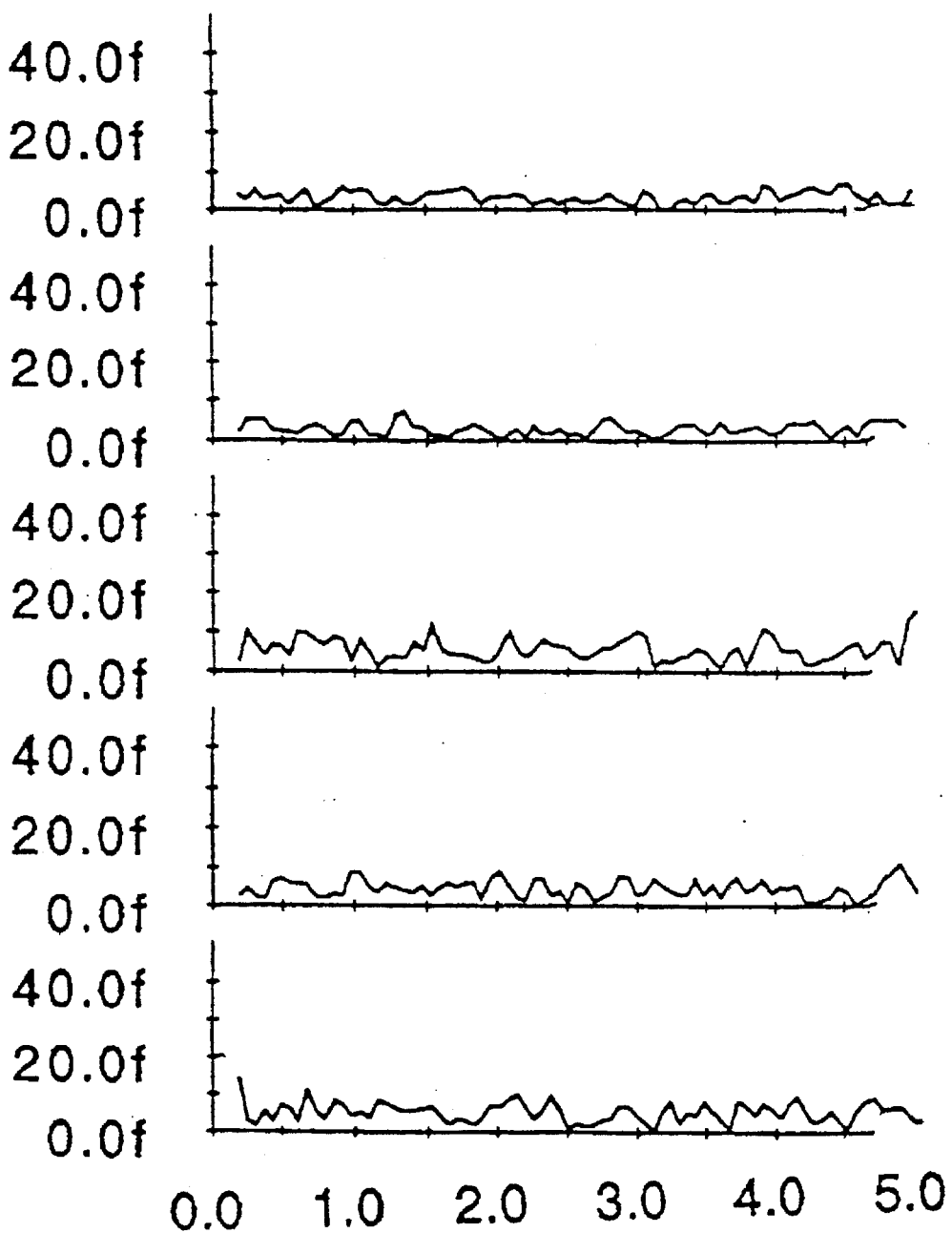
FIG. 29 is a graph similar to FIG. 28 showing low frequency noise data.

Also, the amplitude of this supporting device may be kept to about 2 µm. FIGS. 28 and 29 show data obtained by measuring the noise from a magnetic field assembly (in the absence of a subject) using supporting means according to the invention. It is seen that no noise is produced at 10 ft/√Hz for both low and high frequencies.

As mentioned above, according to the invention supporting pillars of a double housing type support supporting heavy magnetic field-measuring means is anchored onto an H-cross section member of a lattice-like supporting frame, thus allowing a strong "footing" on the floor, to increase the natural vertical frequency to about 10 Hz or greater. The amplitude of the vibration may thus be greatly reduced for a lower level of noise.

The supporting pillars and arms are integrated and are supported in 3 ways by the ceiling, floor and wall of the shielded room. A great reduction in noise is thus possible due to the construction of a secure 3-way support by the wall, ceiling and floor.

Furthermore, with this 3-way support system, the frequency of vibration of the normal mode may also be increased to about 10 Hz or greater in other directions, e.g. in the direction parallel to the arms and in the direction vertical to the arms.

Also, according to the invention, it is possible to further reduce the amount of vibration by using a connecting member to connect the pair of arms supporting the magnetic field-measuring means, and furthermore the arms are provided with the magnetic field-measuring means in a detachable manner, thereby allowing the magnetic field-measuring means to be mounted on the arms in an easily detachable manner, the mounting pieces are provided on the top of the free distal ends of the arms in a detachable manner, and the supporting shaft of the magnetic-field-measuring means is supported by being sandwiched between the arm bodies and the mounting pieces.

Moreover, according to the invention, unwanted vibration may be even further reduced by tapering the top sections of the screws inserted in the supporting pillars and utilizing the wedge action resulting by matching the top sections to depressions whose inner diameter decreases toward the bottom of the arms, to anchor the arms to the supporting pillars.

Further, according to the invention, the proximal ends of the arms may be anchored to brackets with bolts, to further reduce the vibration of the arms. In this manner, the amplitude of the vibration during measurement with the magnetic-field-measuring means is minimized and a reduction in noise may be expected, and consequently the strength of a weak magnetic field generated from a body may be measured at an even higher precision.

In addition, according to the invention, the magnetic-field-measuring means is pivoted on the double housing type support by angular displacement around the horizontal axis at the measuring position to allow tilting, and thus the rigidity of the double housing type support is increased, the frequency of vibration of the normal mode of the magnetic-field-measuring means may be about 25 Hz or greater and the amplitude may be reduced thus avoiding noise contamination. The fact that the subject may be raised and lowered by movement of the bed, eliminating the need for a construction to raise and lower the magnetic-field-measuring means, also allows an increased frequency of vibration of the normal mode and reduced noise.

In addition, according to the invention, the magnetic-field-measuring means may be supported on the double housing type support at the respective magnetic-field measuring and maintenance positions, and the lifting and lowering mechanism for the magnetic field-measuring means is not mounted on the double housing type support, thus resulting in an increased frequency of vibration of the normal mode and reduced noise.

In conclusion, according to the invention, the entire area of the cerebrum and cerebellum of the subject is covered by the magnetic-field-measuring means during measurement of the brain magnetic field, to allow instantaneous measurement of the strength of the magnetic field over the head and to reduce the degree of freedom and range of movement of the supporting means, while allowing the frequency of vibration of the normal mode of the supporting means which supports the magnetic-field-measuring means to be at least about 10 Hz or greater, preferably about 25 Hz or greater and more preferably about 30 Hz or greater, thus reducing the level of noise produced by the vibration and allowing accurate measurement even of brain magnetic fields of about 10 Hz or less.

For example, a brain magnetic field induced by visual or auditory sensing is about 10 Hz, and magnetic fields due to epilepsy at about 2 Hz are usually of as low a frequency as about 1 Hz. These brain magnetic fields may be accurately measured.

Although this invention has been described by way of several embodiments thereof, it should be realized that many alternatives, modifications and variations will be apparent to those skilled in the art of the foregoing description. Accordingly, it is intended to embrace all such alternatives, modifications and all variations as falling within the spirit and broad scope of the appended claims.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A biological information-measuring apparatus which is situated in a shielded room including a ceiling, a floor and a wall, said apparatus comprising:

measuring means for measuring biological information of a subject;

a double housing type support with a pair of supporting pillars for supporting the measuring means disposed therebetween, the supporting pillars each including a top end and a bottom end;

a pair of parallel spaced arms, fixedly disposed between the pair of supporting pillars each arm, having proximal ends and free distal ends and being connected by a connecting member;

a pair of first anchoring means provided on the wall of the shielded room at anchoring positions thereof, the pair of first anchoring means movably anchoring the proximal ends with the wall so that the proximal ends can pivot around a horizontal axis thereof; and displacing means for angularly displacing the measuring means, the displacing means being provided at one of the free distal ends so that the measuring means can pivot around an axis parallel to the horizontal axis of the proximal ends.

2. The biological information-measuring apparatus according to claim 1, further comprising a pair of second and third anchoring means with which the shielded room supports the double housing type support, wherein the second anchoring means anchors the top end of each supporting pillar to the ceiling of the shielded room and the third anchoring means anchors the bottom end of each supporting pillar to the floor of the shielded room.

3. The biological information-measuring apparatus according to claim 1, wherein the measuring means is selected from the group consisting of biomagnetic field-measuring means, MRI means and X-ray CT means.

4. The biological information-measuring apparatus according to claim 1, wherein the biological information comprises biomagnetic field information.

5. The biological information-measuring apparatus according to claim 4, wherein the biomagnetic field information is brain magnetic field information.

6. The biological information-measuring apparatus according to claim 4, wherein the supporting pillars and the pair of parallel spaced arms, collectively, have a frequency of vibration of the normal mode of about 10 $H_z$ or greater.

7. The biological information-measuring apparatus according to claim 1, further comprising a pair of additional anchoring means, provided at the free distal ends of the pair of parallel spaced arms, which detachably anchor the measuring means to the respective arms.

8. The biological information-measuring apparatus according to claim 7, wherein the additional anchoring means comprises a mounting piece detachably formed with the top section, the measuring means includes a supporting shaft attached thereto, and the measuring means is anchored to the arms through the anchoring means such that the supporting shaft is held by the mounting piece and the top section of the free distal end from both sides in a support hole which is formed by the mounting piece and the top section of the free distal end when the mounting piece is in engagement with the top section.

9. The biological information-measuring apparatus according to claim 1, further comprising a pair of additional anchoring means with screws for anchoring the arms to the supporting pillars, wherein the screws penetrate into and engage with the supporting pillars in a direction perpendicular to the axis of the supporting pillars and are tapered to provide a top section thereof, and each arm is provided on a side thereof with a depression, the inner diameter of which becomes smaller as the depression approaches a base thereof, and the top section of each screw fits in the depression to anchor each arm to a respective supporting pillar.

10. The biological information-measuring apparatus according to claim 1, wherein the pair of first anchoring means comprise a pair of brackets and bolts and the proximal ends of the arms are anchored to the brackets using the bolts.

* * * * *